US011713444B2

(12) United States Patent
Talianski et al.

(10) Patent No.: US 11,713,444 B2
(45) Date of Patent: Aug. 1, 2023

(54) NANOCOMPOSITE MATERTAIL

(71) Applicant: CelluComp Limited, Burntisland (GB)

(72) Inventors: Mikhail Talianski, Dundee (GB); Andrew Love, Dundee (GB); Eric Whale, Burntisland (GB); David Hepworth, Burntisland (GB); Natalia Petukhova, Dundee (GB); Jane Shaw, Dundee (GB)

(73) Assignee: CelluComp Limited, Burntisland (GB)

(*) Notice: Subject to any disclaimer, the term of this patent is extended or adjusted under 35 U.S.C. 154(b) by 5 days.

(21) Appl. No.: 15/563,865

(22) PCT Filed: Apr. 1, 2016

(86) PCT No.: PCT/GB2016/050944
§ 371 (c)(1),
(2) Date: Oct. 2, 2017

(87) PCT Pub. No.: WO2016/156878
PCT Pub. Date: Oct. 6, 2016

(65) Prior Publication Data

US 2018/0119235 A1 May 3, 2018

(30) Foreign Application Priority Data

Apr. 2, 2015 (GB) ..................................... 1505767

(51) Int. Cl.

| | |
|---|---|
| ***C12N 1/00*** | (2006.01) |
| ***C08L 1/02*** | (2006.01) |
| ***B82Y 40/00*** | (2011.01) |
| ***C09D 101/02*** | (2006.01) |
| ***C04B 28/02*** | (2006.01) |
| ***C09K 8/467*** | (2006.01) |
| ***C04B 18/02*** | (2006.01) |
| ***C07K 14/005*** | (2006.01) |
| ***C12N 7/00*** | (2006.01) |
| ***C12P 19/04*** | (2006.01) |
| ***B82Y 30/00*** | (2011.01) |
| ***C04B 111/00*** | (2006.01) |
| ***C12R 1/91*** | (2006.01) |

(52) U.S. Cl.
CPC ................ *C12N 1/00* (2013.01); *B82Y 40/00* (2013.01); *C04B 18/022* (2013.01); *C04B 28/02* (2013.01); *C07K 14/005* (2013.01); *C08L 1/02* (2013.01); *C09D 101/02* (2013.01); *C09K 8/467* (2013.01); *C12N 7/00* (2013.01); *C12P 19/04* (2013.01); *B82Y 30/00* (2013.01); *C04B 2111/00482* (2013.01); *C07K 2319/20* (2013.01); *C07K 2319/735* (2013.01); *C12N 2710/00023* (2013.01); *C12N 2710/10031* (2013.01); *C12N 2720/00023* (2013.01); *C12N 2720/00031* (2013.01); *C12N 2770/00023* (2013.01); *C12N 2770/00031* (2013.01); *C12R 2001/91* (2021.05); *Y02W 30/91* (2015.05)

(58) Field of Classification Search
None
See application file for complete search history.

(56) References Cited

U.S. PATENT DOCUMENTS

| | | | |
|---|---|---|---|
| 2009/0221812 A1 | 9/2009 | Ankerfors et al. | |
| 2011/0114244 A1 | 5/2011 | Yoo et al. | |
| 2012/0227800 A1 | 9/2012 | Dang et al. | |
| 2013/0181171 A1 | 7/2013 | Ratna et al. | |
| 2014/0256581 A1 | 9/2014 | Ben-Yoav et al. | |
| 2015/0059617 A1* | 3/2015 | Hepworth | D21H 11/06 106/163.01 |

FOREIGN PATENT DOCUMENTS

| | | | |
|---|---|---|---|
| EP | 2431048 A2 | 3/2012 | |
| JP | 2004-250590 A | 9/2004 | |
| JP | 2007-517500 A | 7/2007 | |
| JP | 2008-094818 A | 4/2008 | |
| JP | 2008-520797 A | 6/2008 | |
| JP | 2011-057832 A | 3/2011 | |
| WO | WO-2005037856 A2 | 4/2005 | |
| WO | WO-2006056737 A1 | 6/2006 | |
| WO | WO-2007104990 A1 | 9/2007 | |
| WO | WO-2011004284 A1 | 1/2011 | |
| WO | WO-2012078069 A1 | 6/2012 | |
| WO | WO-2013128196 A1 | 9/2013 | |
| WO | WO-2013132491 A2 * | 9/2013 | C08K 3/10 |

(Continued)

OTHER PUBLICATIONS

Love, Andrew J., et al., The use of tobacco mosaic virus and cowpea mosaic virus for the production of novel metal nanomaterials., Virology, Elsevier, Amsterdam, NL, vol. 449, Jan. 20, 2014, pp. 133-139.

Niu, Zhongwei, et al., Assembly of Tobacco Mosaic Virus into Fibrous and Macroscopic Bundled Arrays Mediated by Surface Aniline Polymerization, Langmuir, vol. 23, No. 12, Jun. 1, 2007, pp. 6719-6724.

Lee, Seung-Wuk, et al., Virus-Based Fabrication of Mico- and Nanofibers using Electrospinning, Nano Letters, American Chemical Society, US, vol. 4, Mar. 2004, pp. 387-390.

Dumont, Elisabeth, “International Search Report,” prepared for PCT/GB2016/050944, dated Jun. 16, 2016, six pages.

(Continued)

*Primary Examiner* — Robert J Yamasaki
*Assistant Examiner* — Charles Zoltan Constantine
(74) *Attorney, Agent, or Firm* — Winstead PC

(57) ABSTRACT

The present invention relates to nanoparticles and their use to form nanocomposite material, in particular bionanocomposite material, specifically wherein the nanoparticles are formed using plant virus attached to a scaffold of cellulosic material and/or cellulose derived materials, in particular wherein said cellulosic material further comprises plant cell components, for example hemicellulose, pectin, protein or combinations thereof.

12 Claims, 6 Drawing Sheets

Specification includes a Sequence Listing.

(56) References Cited

FOREIGN PATENT DOCUMENTS

| | | |
|---|---|---|
| WO | WO-2013188657 A1 | 12/2013 |
| WO | WO-2014017911 A1 | 1/2014 |
| WO | WO-2014045055 A1 | 3/2014 |
| WO | WO-2014133249 A1 | 9/2014 |
| WO | WO-2014147392 A1 | 9/2014 |
| WO | WO-2014147393 A1 | 9/2014 |

OTHER PUBLICATIONS

Ahsan, A., et al., "Destabilization of the Epidermal Growth Factor Receptor (EGFR) by a Peptide that Inhibits EGFR Binding to Heat Shock Protein 90 and Receptor Dimerization," The Journal of Biological Chemistry, vol. 288, No. 37, Sep. 13, 2013, pp. 26879-26886.

Aljabali, A. A. A., et al., "Virus Templated Metallic Nanoparticles," Nanoscale, 2010, vol. 2, pp. 2596-2600.

Arola, S., et al., "Immobilization-Stabilization of Proteins on Nanofibrillated Cellulose Derivatives and Their Bioreactive Film Formation," Biomacromolecules, 2012, vol. 13, pp. 594-603.

Bendahmane, M., et al., "Display of Epitopes on the Surface of Tobacco Mosaic Virus: Impact of Charge and Isoelectric Point of the Epitope on Virus-Host Interactions," J. Mol. Biol., vol. 290, 1999, pp. 9-20.

Choi, Y. S., et al., "The Mineralization Inducing Peptide Derived From Dentin Sialophosphoprotein for Bone Regeneration," J. Biomed. Mater. Res. Part A, vol. 101, No. 2, 2012, pp. 590-598.

Davie, E. A. C., et al., "Asymmetric Catalysis Mediated by Synthetic Peptides," Chem. Rev., vol. 107, No. 12, 2007, pp. 5759-5812.

Domenyuk, V., et al., "A Technology for Developing Synbodies with Antibacterial Activity," PLoS One, vol. 8, Issue 1, Jan. 2013, p. 1-11.

Gooding, G.V., et al., "A Simple Technique for Purification of Tobacco Mosaic Virus in Large Quantities," Phytopathology, vol. 57, Issue 11, Sep. 1967, pp. 1285.

Love, A.J., et al., "In Planta Production of a Candidate Vaccine Against Bovine Papillomavirus Type 1," Planta, vol. 236, 2012, pp. 1305-1313.

Ruoslahti, E., "RGD and Other Recognition Sequences for Integrins," Annual Review Cell Developmental Biology, vol. 12, 1996, pp. 697-715.

Sidhu, S.S., "Engineering M1 3 for Phage Display," Biomolecular Engineering, vol. 18, 2001, pp. 57-63.

Tan, Y.N., et al., "Uncovering the Design Rules for Peptide Synthesis of Metal Nanoparticles," J. Am. Chem. Soc., vol. 132, 2010, pp. 5677-5686.

Thuenemann, E.C., et al., "The Use of Transient Expression Systems for the Rapid Production of Virus-Like Particles in Plants," Current Pharmaceutical Design, vol. 19, 2013, pp. 5564-5573.

Trifonova, E., et al., "Complexes Assembled From TMV-Derived Spherical Particles and Entire Virions of Heterogeneous Nature," Journal of Biomolecular Structure and Dynamics, vol. 32, No. 8, 2013, pp. 1193-1201.

Turpen, T.H., et al., "Malarial Epitopes Expressed on The Surface of Recombinant Tobacco Mosaic Virus," Nature Biotechnology, vol. 13, Jan. 1995, pp. 53-57.

Vaia, R.A., et al., "Framework for Nanocomposites," Materials Today, Nov. 2004, pp. 32-37.

Wiesner, M., et al., "Peptide-Catalyzed Conjugate Addition Reactions of Aldehydes to Nitroolefins," Synthesis, No. 9, 2010, pp. 1568-1571.

Wiesner, M., et al., "Tripeptides as Efficient Asymmetric Catalysts for 1,4-Addition Reactions of Aldehydes to Nitroolefins—A Rational Approach," Angew. Chem. Int. Ed., vol. 47, 2008, pp. 1871-1874.

Love, A. J., et al., "A Genetically Modified Tobacco Mosaic Virus That Can Produce Gold Nanoparticles From a Metal Salt Precursor," Frontiers in Plant Science, Nov. 10, 2015, vol. 6, Article 984, pp. 1-10.

Office Action for JP Application No. P2017-551667, dated Feb. 4, 2020.

Search Report for Appl. No. GB1505767.2 dated Feb. 5, 2016.

Li, et al., "Effect of Unassembled Phage Protein Complexes on the Attachment to Cellulose of Genetically Modified Bacteriophages Containing Celllulose Binding Molecules," Colloids & Surfaces B Biointerfaces (2010); vol. 76, pp. 529-534.

Tolba, et al., "Oriented Immoblization of Bacteriophages for Biosensor Applications," Applied & Environmental Microbiology (2010), vol. 76, pp. 528-535.

Yang, et al., "A Facile Synthesis—Fabrication Strategy for Integration of Catalytically Active Viral-Palladium Nanostructures into Polymeric Hydrogel Microparticles via Replica Molding," ACS Nano (2013), vol. 7, pp. 5032-5044.

Office Action for Japanese Appl. No. P2017-551667, dated Jan. 26, 2021.

C Kemp-Griffin; "Getting to the roots of rheology: a bio-based thickener that enhances coating performance"; Surface Coatings International; vol. 96 No. 3; Jun. 2013; pp. 160-161.

Sinitsyna, O.V. et al., "Virus-Like Particle Facilitated Deposition of Hydroxyapatite Bone Mineral on Nanocellulose after Exposure to Phosphate and Calcium Precursors", Int. J. Mol. Sci.; 2019, 20: 1814-1825.

* cited by examiner

SEQUENCE LISTING

```
<160> NUMBER OF SEQ ID NOS: 4

<210> SEQ ID NO 1
<211> LENGTH: 44
<212> TYPE: DNA
<213> ORGANISM: Artificial Sequence
<220> FEATURE:
<223> OTHER INFORMATION: MIP3 primer - forward

<400> SEQUENCE: 1

ccggctctga atctgattct tctgattctg attctaagtc tgta                      44


<210> SEQ ID NO 2
<211> LENGTH: 40
<212> TYPE: DNA
<213> ORGANISM: Artificial Sequence
<220> FEATURE:
<223> OTHER INFORMATION: MIP3 primer - reverse

<400> SEQUENCE: 2

tacagactta gaatcagaat cagaagaatc agattcagag                           40


<210> SEQ ID NO 3
<211> LENGTH: 38
<212> TYPE: DNA
<213> ORGANISM: Artificial Sequence
<220> FEATURE:
<223> OTHER INFORMATION: MBP primer - forward

<400> SEQUENCE: 3

ccggctctga aaagctttgg tggggagctt ctcttgta                             38


<210> SEQ ID NO 4
<211> LENGTH: 35
<212> TYPE: DNA
<213> ORGANISM: Artificial Sequence
```

-continued

```
<220> FEATURE:
<223> OTHER INFORMATION: MBP primer - reverse

<400> SEQUENCE: 4

tacaaagaga agctccccac caaagctttt cagag                    35
```

NANOCOMPOSITE MATERTAIL

FIELD OF INVENTION

The present invention relates to nanoparticles and their use to form nanocomposite material, in particular bionanocomposite material, specifically wherein the nanoparticles are formed using plant virus attached to a scaffold of cellulose, cellulosic material and/or cellulose derived materials.

BACKGROUND OF THE INVENTION

Nanoparticles included in polymeric nanocomposites have been an area of increasing interest as industry has sought to improve materials by providing existing materials with additional properties. This has been discussed in for example Richard, A. Vaia and H. Daniel Wagner. Materials Today 2004, 7, 32-37.

Plant viruses and self-assembling components of plant viruses have been discussed as potential nanobuilding blocks that can be used as templates for novel materials and metallic nanoparticles, as discussed by Alaa A. A. Aljabali, J. Elaine Barclay, George P. Lomonossoff and David J. Evans. Nanoscale, 2010, 2, 2596-2600. Whilst functionalised viruses have previously been provided as part of scaffold structures formed of complete whole viruses, this has been limiting in terms of the structures that can be formed.

SUMMARY OF THE INVENTION

The inventors have determined nanomaterials and nanocomposite materials which comprise virus or a virus-like structure (structural components of a virus, for example, not including nucleic acid of a virus or nanoparticles formed from structural components from a virus), wherein the virus or virus-like structure can include peptide sequences or be fused to such peptides or whole proteins (e.g. enzymes) which can enable reactions and/or promote the binding of material to the virus or virus-like structure, or nanoparticles formed from the virus or virus-like structure arranged on a non-virus scaffold material or structure. This enables the scaffold material to be extensively functionalised and allows more controlled nanocomposite material nanostructures or microstructures to be formed. Improved functionality can be provided to the scaffold material by forming a nanocomposite material with for example increased mechanical properties of strength, stiffness or toughness.

The present inventors have determined that virus particles or virus-like particles or other nanoparticles formed by structural components of a virus, in particular plant viruses or bacteriophages or virus-like particles, modified chemically or by genetic means to display particular functional peptides or whole proteins, including enzymes, on their surface, can be used in combination with non-virus substrate scaffolds, for example cellulose derived scaffolds, to provide a scaffold with the virus particles thereon or therein to form nanocomposite material. In particular, the inventors have determined that nanocellulose from plant material can be utilised as a scaffold on to or into which functionalised viruses (and nanoparticles formed therefrom) can be arranged. These nanocomposite cellulosic materials can provide the cellulosic materials with different properties and can be used for a variety of purposes.

Accordingly, a first aspect of the invention provides a nanocomposite material comprising a non-virus scaffold wherein the non-virus scaffold is provided with at least one virus particle modified to display functional peptides on the surface of the virus particle. In particular embodiments, a virus particle and the non-virus scaffold provides a nanocomposite with properties which differ from the properties provided by either the non-virus scaffold or virus particle alone.

In embodiments, functional peptides can be peptide sequences provided on the surface of the virus which allow for a reaction of interest to be enabled, or which allow a particular substrate, ligand or molecule to be bound by the virus, for example antibodies, metal ions, calcium ions or $PO_4^{3-}$. In embodiments, peptide sequences can include whole proteins, in particular enzymes.

Suitably a virus particle may be a virus or a structural component of a virus that can form a virus-like particle or structure or nanoparticle formed therefrom for example a virus particle which is not infectious as it does not include a nucleic acid component, but can surface display a peptide. For example the coat protein of Bovine papillomavirus (BPV) can self assemble into spherical nanoscale structures that can be used to display various functional groups (Love, A. J., Chapman, S. N., Matic, S., Noris, E., Lomonossoff, G. P. and Taliansky, M. E. 2012. In planta production of a candidate vaccine against bovine papillomavirus type 1. Planta 236, 1305-1313). Similarly coat proteins of other viruses such as Cowpea mosaic virus and Human papillomavirus, for example, has such utility. Moreover, some spherical RNA-free nanoparticles can also be formed by coat proteins of rod-shaped viruses, for example Tobacco mosaic virus (TMV)

According to a second aspect of the invention there is provided a process of forming a nanocomposite material comprising a non-virus scaffold wherein the process includes the step of providing a non-virus scaffold with at least one virus particle, virus like particle or nanoparticle therefrom, modified to display functional peptides on the surface of the virus particle. In embodiments, the process of forming the nanocomposite material of the first aspect of the invention, comprises the steps of mixing the scaffold with the modified virus particle to provide a scaffold-virus particle mixture and drying the mixture to form the nanocomposite.

In embodiments a nanocomposite material is a multi-component material wherein one of the components has one, two or three dimensions of less than 100 nm. Typically the nanocomposite will differ markedly from the functionality of the component materials.

Scaffold

In embodiments a scaffold can be a non-virus fibre or structure, for example a polymer rod, carbon nanotube or the like with high aspect ratios, long lengths and controllable widths, for example a length of at least 500 nm, at least 1 micron, at least 2 micron, at least 3 micron, at least 4 micron, at least 5 micron or longer than 5 micron.

In embodiments a scaffold can include two or more non-virus fibres or structures arranged to form a 2-dimensional structure, for example a film-like layer, web-like layer or cross-linked fibre matrix. In embodiments, a two dimensional scaffold can include cross-linked non-virus fibres which provide a large surface area for applications such as separation protocols, concentration protocols, filtration protocols and the like. In embodiments a scaffold can be a polymeric scaffold, comprising linear, branched, hyper branched polymers or combinations thereof.

In embodiments a two-dimensional scaffold structure can be combined with additional two-dimensional scaffold structures to provide a multi-layer film, or a laminate structure. Thus a non-virus fibre and/or two-dimensional scaffold structure can form the building blocks of a 3-dimensional scaffold. In embodiments, a scaffold may be formed by providing a first layer and then forming a second layer over the first layer.

In embodiments the non-virus scaffold can comprise an organic or inorganic scaffold. In particular examples, the scaffold can comprise carbon fibre, carbon nanotubes, glass fibres, silk fibres, aramid fibres, hemp fibres, or flax fibres or a combination thereof. In embodiments the non-virus scaffold can comprise plastics or ceramics.

In embodiments the non-virus scaffold can comprise an organic substrate, for example an organic polymer, for example in embodiments the non-virus scaffold can comprise a natural fibre polymer. In embodiments, the natural fibre polymer can comprise plant fibres such as coir, hemp, jute, wood fibre, sisal, straw, cellulose or the like. In embodiments, the scaffold can comprise cellulosic materials, for example a derivative of cellulose, cellulose nanoparticles, cellulose microfibrils or nanocrystals.

It will be understood by those of skill in the art that such cellulosic materials will differ from microcrystalline cellulose. Suitably, in embodiments, the cellulosic material discussed herein differs from microcrystalline cellulose in that the cellulosic material comprises further components of the plant cell wall from the plant material from which the cellulosic material is derived for example further comprises hemicellulose, pectin, protein or combinations thereof. This will be apparent from the methods used to extract the cellulosic material. In suitable embodiments, the plant cell wall material can comprise cellulose, hemicellulose (such as xyloglucans, xylans, mannans and glucomannans), pectins, and proteins such as glycoproteins. In such embodiments, a scaffold material can include plant cells, plant cell walls or portions thereof, associated plant cell polymeric components or combinations thereof, for example the scaffold comprising cellulosic material may comprise cellulose, hemicellulose, pectin and protein.

In embodiments the scaffold can be a monolithic structure. In other embodiments the scaffold can be a laminate structure. In further embodiments, the scaffold can be a fibrous or filamentous or lattice structure. Suitably, the virus particles and nanoparticles thereof may bind to the scaffold such that they provide an ordered monolayer or monolayers through the scaffold. Alternatively, the virus particles and/or nanoparticles thereof may be distributed throughout all or part of the scaffold. The distribution of the virus particles in or on the scaffold may be influenced by the provision or application of the virus particles and nanoparticles thereof to the scaffold.

A non-virus scaffold for use in the invention can be produced by a number of different processing routes. For example, if the non-virus scaffold comprises cellulose or cellulosic materials then it can be produced from woody plants e.g. trees or herbaceous plants e.g root vegetables. A range of extraction methods can be used to produce the cellulose scaffold depending upon the nature of the starting material and the desired end product. For example, extraction methods to produce a cellulose scaffold from herbaceous plant material will typically differ from extraction methods based on root vegetable starting materials. However, the extraction methods may generally comprise the steps selected from 1) Acid extraction—e.g. 0.3 M sulphuric acid at between 50 and 90° C., 2) Alkali extraction—e.g. 0.1-1 M NaOH at 90° C., 3) Enzyme extraction, 4) hydrogen peroxide extraction at 90° C., 5) bleach extraction e.g. Sodium hypochlorite at 60° C., 6) heat treatment at 90-110° C. 7) homogenisation,—high shear or high pressure.

Cellulose nanofibres can also be produced from bacteria. This is known as bacterial cellulose. Culture of the bacteria can allow production of quantities of cellulose material with a nanofibre structure WO2014133249 (A1). For example, a suitable microbial strain may be cultured in a medium to prepare a first cellulose gel. This cellulose gel may be pulverized to obtain micronized cellulose. The micronized cellulose may be allowed to undergo a gelation step to obtain a second cellulose gel. In embodiments, the second cellulose gel may have a more micronized fiber length but similar moisture content or density as compared with the first cellulose gel.

These methods may be used individually or in combination depending upon the desired purity of the cellulose and the desired particle size of the end cellulose product used to form the scaffold. In many cases it can be an advantage to have impure cellulose as the other cell wall components can add useful functionalities. For example, it has been determined to be advantageous for rheological formulations if hemicelluloses such as xyloglucan are still present in significant amounts in the extracted material. It is considered these additional polymers may provide better hydrogen bonding sites than the cellulose alone.

Cellulosic materials which can act as a scaffold structure can be made by a number of different process routes and result in materials with different purities of cellulose and different structural units. In suitable embodiments, the cellulosic material is provided such that it includes components of the plant cell wall rather than cellulose alone, for example the cellulosic material can comprise cellulose, hemicellulose (such as xyloglucans, xylans, mannans and glucomannans), pectins, and proteins such as glycoproteins. In such embodiments, the cellulosic material can include plant cells, plant cell walls or portions thereof, associated plant cell polymeric components or combinations thereof, for example the scaffold comprising cellulosic material may comprise cellulose, hemicellulose, pectin and protein. In embodiments the cellulosic material comprises parenchymal cellulose, a particulate cellulose material containing by dry weight of the particulate cellulosic material, at least 70% cellulose, less than 10% pectin and at least 5% hemicellulose wherein the particulate material has a volume-weighted median major particle dimension in the range 25 to 75 micrometer, preferably in the range 35 to 65 micrometer as measured by light diffractrometry. Preferably the particles have a diameter of less than 120 micrometers, more preferably less than 110 micrometers.

As used herein, nanocellulose is broadly defined to include a range of cellulosic materials and derivatives of cellulose, including but not limited to microfibrillated cellulose (cellulose microfibrils), nanofibrillated cellulose, microcrystalline cellulose, nanocrystalline cellulose (cellulose nanocrystals), and particulated or fibrillated wood derived pulp. Typically, nanocellulose as provided herein will include particles having at least one length dimension (e.g. diameter) on the nanometre scale. Nanocellulose, nanofibrillated cellulose or cellulose nanofibrils as used herein also encompass cellulose fibers or particles which can be nano-meter sized or have both micron and nanometerisized portions.

In embodiments nanocellulose can be provided from wood processing. In embodiments the nanocellulose can be provided from waste plant material. In embodiments the plant material may be selected from carrot, turnip, swede, apple, sugar beet, beetroot, potato or onions.

Suitably, nanocellulose may be provided by mechanically shearing fibres to liberate microfibrils. Mechanical shearing may be achieved by high pressure homogenization or high shear homogenisation Suitably pre-treatments, such as mechanical cutting, acid hydrolysis, alkaline treatment, enzymatic pretreatments, carboxymethylation, bleach treatment, hydrogen peroxide treatment or 2, 2, 6, 6-tetramethylpiperidine-1-oxyl (TEMPO)-mediated oxidation may be utilised.

Suitably the cellulose microfibrils or nanoparticles or nanocrystals of cellulose provided therefrom may be used to form a scaffold of the present invention. In embodiments, the cellulose microfibrils or nanoparticles may be chemically modified on their surface to alter one or more of their surface hydroxyl groups.

In embodiments the cellulose scaffold can be formed from fibrillated plant fibres. That is plant fibres that have been chemically and mechanically treated to partially separate the microfibrils within the fibre structure. This effect may just be on the surface of the fibres or penetrate deeper into the structure.

In embodiments a cellulose scaffold may be formed from cellulose platelets of micron size, but with nanoscale structure within said platelets. In embodiments the non-virus scaffold structure can comprise a plurality of cellulose fragments with each fragment made from a network of cellulose microfibrils and for example the cellulose fragments by close association can make up a larger network of cellulose microfibrils through the body of the material. In embodiments the non-virus scaffold can comprise herbaceous plant tissue heat treated and homogenised to provide a scaffold of cell wall material. In embodiments the cellulose scaffold can be formed from cellulosic material as discussed herein (for example comprise further components of the plant cell wall from the plant material from which the cellulosic material is derived, suitably, the plant cell wall material can comprise cellulose, hemicellulose (such as xyloglucans, xylans, mannans and glucomannans), pectins, and proteins such as glycoproteins), in particular the cellulose scaffold can comprise parenchymal cellulose, a particulate cellulose material containing by dry weight of the particulate cellulosic material, at least 70% cellulose, less than 10% pectin and at least 5% hemicellulose wherein the particulate material has a volume-weighted median major particle dimension in the range 25 to 75 micrometer, preferably in the range 35 to 65 micrometer as measured by light diffractrometry. Preferably the particles have a diameter of less than 120 micrometers, more preferably less than 110 micrometers.

In embodiments a cellulose scaffold can be formed from individualised cellulose nanofibres.

In embodiments the non-virus scaffold structure can comprise a biocomposite material comprising a plurality of cellulose fragments made up of a network of cellulose nanofibres/microfibrils, one or more hydrophilic binders located within the network of cellulose nanofibres/microfibrils and one or more hydrophobic binders arranged to interact with the hydrophilic binders so as to encapsulate the plurality of cellulose fragments as described by International patent application WO2006/056737. In such embodiments, the hydrophilic binders can comprise a hydrophilic or substantially hydrophilic polymer. The hydrophilic polymer may comprise a hemicellulose, an acrylic resin or alternatively a partially hydrolysed polyvinyl acetate. Optionally the hydrophilic polymer can comprise a biological hydrophilic polymer e.g. gelatine and guar gum.

Optionally the hydrophobic binders can comprise a hydrophobic polymer. The hydrophobic polymer may comprise an epoxy such as a bisphenol-A or a modified bisphenol A epoxy. Alternatively the hydrophobic binder can comprises a binder selected from the group comprising polyurethanes, phenolic resins, acrylics and siloxanes. Other suitable hydrophilic and hydrophobic binders would be known to those of skill in the art.

In embodiments the non-virus scaffold structure can comprise a fibre reinforced material comprising a biocomposite material reinforced with a plurality of fibres wherein the biocomposite material comprises one or more of cellulose fragments made up of a network of cellulose microfibrils one or more hydrophilic binders located within the network of cellulose microfibrils/nanofibers and one or more hydrophobic binders arranged to interact with the hydrophilic binders so as to encapsulate the plurality of cellulose fragments as described by international patent application WO2007/104990.

In embodiments the non-virus scaffold structure can comprise cellulose platelets with diameter greater than 10 microns and thickness less than 1 micron, characterised in that the cellulose platelets comprise at least 60% cellulose by dry weight, less than 10% pectin by dry weight and at least 5% hemicellulose by dry weight as described by international patent application WO2013/128196.

In embodiments, the non-virus scaffold structure can comprise plant-derived cellulose particulate material comprising less than 30 wt % extractable glucose; and extractable xylose in an amount of at least 5% of the amount of extractable xylose in the starting plant material. Suitably, in such embodiments the plant-derived cellulose particulate material comprises less than 60 wt % cellulose. This material was produced as described in the Rheological Material example provided in the examples section herein and the extractability of the components was determined by using an acid hydrolysis method as set out herein. Suitably a material may be provided using a method as set out in WO2014/147392 or WO2014/147393.

In embodiments the plant derived cellulose particulate material can comprise extractable xylose in an amount of from 5% to 10% of the amount of extractable xylose in the starting plant material, as defined by an extraction technique of acid hydrolysis as described herein.

In embodiments the plant derived cellulose can be a cellulose microfibrillated material in which regions of amorphous cellulose and associated mechanical properties are retained, rendering the material suitable for use in high performance composite materials. The cellulose microfibrillated material can be characterized also by retaining one or more matrix polysaccharides. Thus, the material can comprise cellulose microfibrils and one or more matrix polysaccharides selected from homogalacturonan, (1→4)-β-D-(galacto)mannan, (1→4)-β-D (galacto)(gluco)mannan, (1→4)-β-D-(gluco)mannan, (1→4)-β-D-galactan, xyloglucan, (1→4)-β-D-xylan and (1→4)-β-D-arabinoxylan.

The process for preparing cellulose microfibrils from herbaceous plant material can comprise: contacting the herbaceous plant biomass with a single enzyme or an enzyme composition comprising at least one endo-glucanase; and/or one or more polysaccharide hydrolases from endo polygalacturonase, arabinofuranosidase pectin lyase, pectate lyase, pectin methyl esterase, endo-arabinanase, endo-galactanase, galactosidase, rhamnogalacturonan hydrolase, rhamnogalacturonan lyase, or xylanase to form an enzyme-treated biomass; and mechanically processing the enzyme-treated biomass to produce cellulose microfibrils. Such a process is described for example in US 2009221812(A1), WO2013/188657 A1, WO2011/004284 A1.

In embodiments of the process, the scaffold can be provided to the virus, virus-like particle or virus-derived nanoparticle as a solid. In alternative embodiments, the scaffold can be provided to the virus or nanoparticle as a liquid. In embodiments, the solid scaffold can be a dried version of a liquid scaffold composition, possibly with the addition of resins/binders so it forms a composite. Resin binders may advantageously enhance strength, stiffness, toughness and also water resistance of the scaffold. Where the scaffold composition is provided as a liquid, for example a liquid cellulose platelet composition, in particular, wherein the composition is defined by xylose extractability or with respect to rheology modifiers such a scaffold composition can be added to water based systems such as paint formulations and be easily dispersible. It is considered the incorporation of metal particles into these scaffold compositions will increase the functionality of the composition e.g dispersible catalysts or dispersible rheology modifier with biocidal action.

In alternative embodiments, nanocomposite materials can be formed by attaching the virus to a cellulose scaffold, then drying or partly drying the scaffold in a way that enables it to retain good porosity. The scaffold structure can then be permeated with water including a metal salt through the part dried scaffold. It is considered this methodology could speed up the concentration of the metal particles on the scaffold.

In embodiments the scaffold can be modified to provide virus particle binding regions thereon. For example, the scaffold substrate may be functionalised in or on the substrate to provide regions to which the virus particles or nanoparticles thereof can bind. Alternatively, the virus particles may be modified to provide the virus particles with scaffold substrate binding functionality on the surface of the virus.

Suitably, the virus particles or nanoparticles thereof may be bound to the scaffold structure by covalent binding. Suitably, the virus particles may be bound to the scaffold structure by non-covalent bonds, for example, hydrophobic interactions, hydrogen bonding, Van der Waal forces and the like. Advantageously, in embodiments neither the virus particles nor the scaffold require any modification to provide for binding of the virus particles to the scaffold.

In embodiments, a nanocellulose scaffold with virus particles or nanoparticles thereof on or in the scaffold may provide enhanced mechanical properties over a cellulose scaffold not including virus or nanoparticles therefrom when the material is dried, for example increased stiffness, strength and toughness. Suitably, cellulose nanofibres can have stiffness greater than 100 GPa and strength greater than 2 GPa, which is of the order of carbon fibre materials. In embodiments, a nanocellulose scaffold can be porous, with the distance between nanofibres in such a scaffold being of the order of 100 s of nm. Suitably, in such embodiments, pore size can be controlled for example by controlled drying methods. In embodiments, freeze drying may be used to provide pores in the scaffold. In embodiments slow air drying may be used to provide pores in the scaffold, for example, air drying at room temperature (10-30° C.) over a period of 0 to 24 hours. Freeze drying typically will provide larger pores than air drying.

Virus

A virus particle or structural components thereof, for example a virus-like particle which does not comprise nucleic acid which can be provided to the scaffold may be modified by any suitable means known in the art, in particular the virus particle or virus-like particle may be modified chemically or by genetic means. Suitably, in embodiments virus particles or virus-like particles can be genetically modified to surface display a functional peptide, or alternatively a chemical approach can be taken to covalently or non-covalently link a functional peptide or whole protein (enzyme) to a particular residue(s) on the viral surface (i.e. EDC/NHS linkages of N-terminal carboxybenzyl protected peptides to lysine groups, for example). A functional group may be provided on the surface of the virus particle or virus-like particle, for example wherein the functional group enables the virus particle to bind to and reduce metal salts or the like.

Examples of suitable virus particles include non-enveloped viruses having a capsid coat such as a helical capsid, a filamentous capsid, or an icosahedral capsid. In embodiments the virus particle can be selected from a helical (rod shaped) virus including tobacco mosaic virus (TMV), tobacco rattle virus (TRV), barley stripe mosaic virus (BSMV), and peanut clump virus (IPCV); a filamentous virus such as citrus tristeza virus (CTV), ebola virus and potato Virus X (PVX), or an icosahedral virus such as bovine papillomavirus (BPV), potato leaf roll virus (PLRV), cowpea mosaic virus (CPMV), polio virus, cauliflower mosaic virus (CaMV), blue tongue virus or the like or other nanoparticles formed by structural components of viruses, for example spherical particles formed by coat protein of rod-shaped tobacco mosaic virus.

In particular embodiments the virus particle can be a tobacco mosaic virus (TMV) particle. In alternative embodiments the virus particle can be bacteriophage. In embodiments the bacteriophage can contain linear dsDNA (Rudiviridae and Podoviridae), circular dsDNA (Bicaudaviridae and Corticoviridae), circular single stranded DNA (Microviridae), linear ssRNA (Leviviridae) or dsRNA (Fuselloviridae). In embodiments, bacteriophages of utility for this invention can have isometric (Corticoviridae), lemon-shaped (Fuselloviridae), ovoid (Guttavirus), bottle-shaped (Ampullaviridae), rod-shaped (Rudiviridae), filamentous (Inoviridae) and pleomorphic (Plasmaviridae) morphologies. In embodiments, bacteriophage of utility may have (Myoviridae) or may not have contractile tails (Siphoviridae). Suitably, such a bacteriophage may be modified to display peptides. For example, the M13 filamentous bacteriophage has an external surface comprising 2700 copies of the major coat protein (P8) arranged around a nucleic acid which is capped at one end with a surface exposed array of P9 and P7 proteins, with the other end covered with P3 and P6 proteins. In such an example, using techniques as known in the art (Sidhu SS. 2001. Engineering M13 for phage display. Biomol Eng. 2001 September; 18(2):57-63), the coat proteins may be modified to contain additional functionalities).

In embodiments the virus particle or nanoparticle formed therefrom can be sized between about 5 nm to about 900 nm, suitably from about 10 nm to about 900 nm, suitably from about 20 nm to about 500 nm, in particular about 350 nm, in particular about 100 nm, in particular about 85 nm, or about 10 nm to about 50 nm, or greater than 15 nm, greater than 25 nm, greater than 30 nm, greater than 40 nm, greater than 50 nm, greater than 70 nm, or greater than 80 nm. In embodiments, the virus particle can have dimensions of 18 nm to 900 nm, suitably 18 nm to 300 nm, in particular 300 nm to 900 nm for example.

In embodiments nanoparticles formed from a virus particle can have a shape selected from, for example, a sphere, rod, prism, hexagonal and mixed prism and other shapes.

The virus particle may suitably be provided on or in the non-virus scaffold wherein the scaffold acts as a template structure to locate a virus particle. In embodiments functionalization of the virus particle can allow the surface displayed peptides of the virus particle to reduce metal ions to allow production of a metallic nanoparticle. In other embodiments, functionalisation of the virus particle can allow the surface displayed peptides of the virus particle to bind calcium and/or phosphate or allow the linkage of another element or substance to the virus particle, for example the covalent linkage of an antibody or fragment thereof. Suitably, the virus particle may be modified to provide the virus particle with a reactive group on the surface of the virus particle. Chemical modification, functionalization and/or genetic modification may be utilised to modify the amino acids of the coat protein of the virus particle exposed on the outer surface of the particle. Additionally, or alternatively, chemical modification, functionalization and/or genetic modification may be used to modify the virus particle internal cavity environment. Substances may be provided on the virus particle or to a functionalised virus particle prior to incorporation of the virus particle into or onto the scaffold. Alternatively, the virus particle may be provided in or on the scaffold and then provided with the substance, for example metal ion, phosphate or calcium ion. As will be appreciated, a virus particle can include multiple copies of a peptide on its surface and thus the virus particle may be functionalised through the addition of at least 10, at least 20, at least 30, at least 50, at least 100, at least 200, at least 300, at least 400, at least 500, at least 1000, at least 1500, at least 2000, at least 2500 peptides per virus particle.

In embodiments, a virus particle can be a plant virus particle. In embodiments the plant virus particle can be modified at its surface through the addition of a peptide able to bind to metal, able to bind phosphorous ($PO_4^{3-}$), able to bind calcium ($Ca^{2+}$) or other bone minerals, able to provide reducing activity and/or able to act as a catalyst.

In embodiments, a virus particle, in particular a plant virus, can be modified to provide a functional tripeptide Pro-Pro-Glu on its surface, wherein the functional tripeptide can act as an effective catalyst for conjugate addition reactions between aldehydes and nitroolefins (Such reactions are discussed, for example by Wiesner M, Wennemers H. Peptide catalyzed conjugate addition reactions of aldehydes to nitroolefins. Synthesis 2010, 1568-1571; Wiesner M, Revell J D, Wennemers H. Tripeptides as efficient asymmetric catalysts for 1,4-addition reactions of aldehydes to nitroolefins—a rational approach. Angew. Chem. Int. Ed. β, 47:1871-1874). In alternative embodiments, peptides can be provided on a virus particle suitable to combine an enolate with an aldehyde or ketone to yield a β-hydroxycarbonyl compound, or to provide for addition of ketones to nitroolefins. In alternative embodiments, peptides may be provided on a virus particle, wherein the peptide can act as competent N-heterocyclic carbene organocatalysts in the intramolecular Stetter reaction, and also as catalysts in oxidation, sulfinyl transfer and phosphorylation reactions Davie EAC, Mennen S M, Xu Y, Miller S J. Asymmetric Catalysis Mediated by Synthetic Peptides. *Chem. Rev.,* 2007, 107 (12), pp 5759-5812]. In alternative embodiments, the virus particle may be provided with peptides with the capacity to sequester anions and cations and possess the ability to reduce various ions. The peptides may also have functional biological activities such as antimicrobial capacities as for example discussed in Domenyuk V, Lushkutov A, Johnston S A, Diehnelt C W. 2013. A technology for developing synbodies with antibacterial activity. PLoS One, 1, 8., such that these can be included, ligand/receptor binding (antibodies for example), cell adhesion factor activity, for example the RGD peptide which permits integrin binding (Ruoslahti E. RGD and other recognition sequences for integrins. 1996. Annual Review Cell Developmental Biology, 12: 697-715), and cell growth/differentiation capacity (for example the peptide named disruptin can degrade the epidermal growth factor receptor and inhibit tumour growth (Ahsan A, Ray D, Ramanand S G, Hegde A, Whitehead C, Rehemtulla A, Morishima Y, Pratt W B, Osawa Y, Lawrence T S, Nyati M K. 2013). Destabilization of the epidermal growth factor receptor by a peptide that inhibits EGFR binding to heat shock protein 90 and receptor dimerization. (The Journal of Biological Chemistry, 288, 26879-26886.). In a further embodiment, the virus particle can comprise peptides with the capacity to strongly bind phenolics, which may have applications in binding dyes (tannins and anthocyanins) and sequestering antioxidant polyphenolics, for example phenolic binding peptides, as described in EP 2431048.

In particular embodiments, a virus particle may be provided with metal binding and reducing peptides on the surface of the particle. Advantageously, such virus particles could be used to incorporate a metal into a non-virus scaffold, for example an organic scaffold, suitably a cellulose or cellulosic material scaffold, in particular a nanocellulose scaffold. In an embodiment, the metal binding and reducing peptides of the virus particles, when bound on the scaffold, can be mixed directly with metal salts in order to produce metallized networks. Suitably, in such embodiments, metal salts or other inorganics may be passed through the scaffold, for example a matrix of cellulose or cellulosic material and virus to provide for the rapid accumulation of inorganic material. In an alternative embodiment, the virus particles with surface displaying metal binding peptides may be attached to the metal or metal ion to form the metal nanoparticles (or metallized viruses) prior to incorporation into the scaffold, for example a cellulose/cellulosic material scaffold, in particular nanocellulose matrix.

In embodiments the inclusion of metal binding and reducing peptides on the surface of a virus particle can be used to provide virus particles, for example TMV modified virus particles, on a scaffold such as a nanocellulose scaffold. The scaffold (nanocellulose scaffold) including the virus particles can then be mixed or provided to a metal salt solution, for example a silver salt solution such that the metal nanoparticles, for example silver nanoparticles, are provided in the scaffold for example nanocellulose scaffold.

In embodiments a metal ion, which can be reduced, or a metal can be bound by a peptide provided on the surface modified virus particle. The metal ion or metal can be selected from the group comprising transition metals including Al, Ga, In, Ge and Sn, silver, gold, iron, copper, indium, platinum, palladium, rhodium, manganese, zinc, molybdenum, iridium, cobalt and the like, suitably selected from silver, gold, iron, indium, platinum, palladium, rhodium, cobalt or iridium.

Suitably, a virus particle may be provided with a peptide on the surface modified virus such that it can provide a reduction potential in the range 1.5 V to −0.44 V. For a given peptide it would be expected that conversion from metal ions into metal nanoparticles would favour those metals with positive reduction potentials. The reducing capacity for a given peptide can be tested using various antioxidant assays (such as FRAP). In embodiments, TMV functionalized with the MBP peptide (metal reducing and binding) can produce metal nanoparticles from metal ions with reduction potentials of 1.5 V (gold (III)) to −0.44 V (iron(II)).

Metal binding and metal ion binding and reducing peptides attached to the virus not only allow the formation of nanoparticles, but can allow metals to be preferentially deposited on the scaffold, for example a metal coated virus particle to be provided on or in a nanocellulose matrix. Cobalt, gold and silver coated virus particles attached to a scaffold, for example a cellulose or cellulosic material scaffold for example nanocellulose matrix can be provided to enable chemical catalysis; for example gold functionalization may facilitate carbon-carbon coupling reactions or alcohol or CO oxidation, silver functionalization may promote $CO_2$ conversion to CO. Platinum or cobalt functionalization/coatings may facilitate water photolysis for hydrogen gas evolution in fuel cells.

In alternative embodiments, the virus particles may be provided with $PO_4^{3-}$ and/or $Ca^{2+}$ binding peptides on the surface of the particles. Advantageously, such virus particles could be used to incorporate a phosphate and/or calcium into a non-virus scaffold, for example an organic scaffold, in particular a nanocellulose scaffold to allow for deposition of bone minerals (hydroxyapatite, HA). This would allow the production of scaffolds which can resemble networks or matrices coated in bone minerals which may be utilised in bone repair and/or tissue engineering. Such nanocomposites may be useful in promoting osteogenesis including cell ingression and binding into scaffold structures.

In embodiments the virus particle can be any non-enveloped virus particle whether or not the particle is infectious. In embodiments the virus can be a plant virus.

In particular embodiments the functional groups displayed on the viral surface can have metal chelating and reducing capacity, or antimicrobial activities or $Ca^{2+}$ and phosphate sequestering and binding activities. Such functionalities could be used for production of metal nanoparticles/metal coated surfaces (nanoparticle synthesis and new types of battery), antimicrobial coatings (antibiofilm and disinfectant surfaces) and bone repair applications respectively, when the decorated viruses are incorporated into said nanocellulose matrix.

Other viruses such as phages may be similarly exploited to surface display functionalities. It has been determined that viruses may be bound in or onto the scaffold for example cellulose or nanocellulose without requiring alteration of the virus. Binding is considered to occur by any suitable means, such as hydrogen bonding, metal coordination, Van der Waals and/or hydrophobic interactions or a combination of bonding. In embodiments, the incorporation of the virus into the matrix may be promoted by using particular formulations of nanocellulose which are conducive for said bond formation to the virus. In further embodiments inclusion of cellulose binding peptides into the viral structure may be used to promote interaction of the virus with cellulose scaffolds, for example nanocellulose scaffolds. In embodiments, covalent linkages between the virus and nanocellulose can be facilitated via chemical approaches as would be known in the art, for example, according to Arola et al. 2012 (Arola S, Tammelin T, Setala H, Tullila A, Linder M B. 2012. Immobilization-Stabilization of Proteins on Nanofibrillated Cellulose Derivatives and Their Bioactive Film Formation. Biomacromolecules 2012, 13, 594-603). In embodiments the virus may have cellulose or nanocellulose binding activity with other functionalities ascribed to it (produced using current art genetic and chemical methods), which in turn can bind to cellulosic structures and impart desired reactivities and other physical and chemical properties to the matrix. In embodiments different nanocellulose compositions, chemical modification of nanocellulose, and various chemical and genetic modifications of virus structures may be used combinatorially to create nanocellulose with desired characteristics.

Other nanoparticles formed by structural components of viruses such as spherical particles formed by the coat protein of tobacco mosaic virus (patent WO2012078069 A1; Trifonova E, Nikitin N, Gmyl A, Lazareva E, Karpova O, Atabekov J. Complexes assembled from TMV-derived spherical particles and entire virions of heterogeneous nature. J Biomol Struct Dyn. 2014; 32(8):1193-1201) may also be similarly exploited to surface display functionalities. It has been determined that such nanoparticles can covalently or non-covalently bind various functional peptides or whole proteins (enzymes).

The functionalized virus and virus-like structures (coat proteins that have self-assembled into viruses or other nanoparticles, but are devoid of nucleic acid) used in the invention which may be produced using plants, bacteria, yeast or insect cells (as discussed by WO2014/045055), can generate from chemical precursors, nanoparticles that may be incorporated into the scaffold substrate; thus forming scaffolds decorated or embedded with nanoparticles. In addition or alternatively the functionalized viruses and virus-like particles may be incorporated into the scaffold substrate to confer novel functions such as promoting metal deposition on the scaffold substrate or formation of free metal nanoparticles distal to the substrate surface after application of precursors. Unlike previous methods of forming nanoparticles for use with a scaffold, this novel approach permits the formation of metal nanoparticles or metallized matrices in a manner which does not require addition of hazardous chemicals (sodium borohydride for example) or fresh plant extracts for reduction of chemical groups into nanoparticle forms.

With regard to Ca and $PO_4$ ions, cellulose scaffolds, for example nanocellulose scaffolds containing virus functionalized with the hydroxyapatite forming peptide (MIP3) have been determined to lead to significant and regulated deposition of HA into the cellulose, for example nanocellulose scaffold. Such nanocomposites comprising a cellulose scaffold, in particular nanocellulose and virus functionalized with hydroxyapatite forming peptide (MIP3) can be used for applications in bone tissue engineering.

A virus particle provided on a non-virus scaffold allows the inclusion of the nanoscale particles in or on the scaffold substrate. Advantageously, the use of virus particles allows such nanoscale particles to have a defined and homogeneous size distribution. By homogeneous is meant the majority of the particles in a sample are substantially the same size. Further, the nanoscale particles may have a homogeneous shape, wherein the majority of the particles are of substantially the same shape. In embodiments, the method of virus attachment to the scaffold can enable the distance between nanoparticles to be controlled, allowing functional porosity of the scaffold to be controlled.

In embodiments to form the functionalised virus scaffold structure, a concentration of 100 ng to 10 mg of virus can be utilised per 250 μl of scaffold substrate, for example a cellulose scaffold. In embodiments, 220 μg of virus per 250 μl of nanocellulose may be utilised. As will be appreciated by those of skill in the art, in particular applications a low concentration of virus particles may be provided to the scaffold substrate, such that the virus particles are provided spaced apart on the scaffold, for example metal catalysts may only be required at very low concentrations, for example at 100 ng per 250 μl. Alternatively, biocides may only require to be provided at very low concentrations, for example at 100 ng per 250 μl, on a scaffold substrate. In embodiments, wherein a nanocellulose scaffold is utilised, and the scaffold is formed of platelets of cellulosic material, virus may be preferentially located on the outside of the platelets. Also we might be able to come up with clever methods that would make them locate either in or outside platelets depending upon requirements.

In embodiments the virus can be added directly to the scaffold structure, for example, cellulosic material, or nanocellulose and then immediately dried, for example air dried.

In embodiments, the process may further comprise the step of incubating the mixture prior to drying. Suitably, the virus and scaffold structure may be stored/incubated for hours, days or weeks in the temperature range 0-25° C. to provide a scaffold structure virus particle mixture. In some cases incubation time may be required to allow virus/scaffold structure, for example a cellulose or cellulosic material, in particular nanocellulose, associations to occur. In embodiments, incubation at temperatures around 25° C. and higher may lead to bacterial or fungal contamination after prolonged time. Alternatively the virus/cellulose, in particular cellulosic material or nanocellulose mix may be incubated at 25° C. to 60° C., 25° C. to 70° C., 25° C. to 80° C. or 25° C. to 90° C., for varying durations. For example tobacco mosaic virus is still stable after heating to 80° C. and thus functionality should be preserved at this temperature.

To form a scaffold structure-virus particle mixture, mixing techniques such as shaking, stirring, vortexing, inversion, and low amplitude sonication (this will be less likely to shear and potentially alter the structure and functionalities of the virus and cellulosic material in particular nanocellulose) could be used. In other situations mixing may not be required, as viruses may adhere to the surface of the already formed dried cellulose, in particular a cellulosic material or nanocellulose membrane via the action of cellulose binding peptides (if required in a particular instance).

In embodiments, a scaffold may be formed by weaving or lamination of the scaffold material to locate the virus particles at particular portions of the weave or lamination. In embodiments, the scaffold may comprise fibres and the fibres, for example cellulose, in particular cellulosic material or nanocellulose fibres, can be spun and woven to form a scaffold with a 3 dimensional structure. In such embodiments if the virus particles are provided on the fibres then the fibres can be spun into threads, and scaffold structures and materials can formed by weaving methods. In embodiments printing or arraying can be used to form the structure and functionalities at the micronscale level, thus leading to production of materials with particular characteristics.

According to a third aspect of the present invention there is provided the use of the nanocomposite of the first aspect of the invention or as provided by the process of the second aspect of the invention in at least one of paint, coatings, concrete, drilling fluids, optoelectronics, pharmaceuticals, biomedicine, as catalysts or catalyst supports, fuel cell technology, bioreactors, electrolyte membranes, sensor technology in particular biochips, 3D scaffold material for tissue repair, cosmetics, bone repair, and personal care products.

In embodiments, a scaffold can be used to display a range of different modified virus particles wherein the different modified viruses can provide at least two different functionalities to the scaffold. The scaffold with functionalised virus, or a virus nanoparticle thereof, in or on the scaffold may be overlaid on top of another scaffold to create a matrix with different functional regions. For example in embodiments a first scaffold layer can be functionalized with proteins and peptides attached to a virus which inhibit biofilm formation on the scaffold, and a second scaffold layer, functionalised with virus wherein the virus contains antimicrobial peptides that can actively kill bacteria, can be provided adjacent to the first scaffold layer. In such an example a filter for killing microbes in water and other solutions can be formed. Alternatively, a scaffold, for example a cellulose or cellulosic material, in particular nanocellulose scaffold, can be coated with hydroxyapatite (HA) via viruses attached to the scaffold wherein the viruses are functionalised such that they sequester Ca and $PO_4$ ions. This scaffold may be further functionalized using viruses which display both HA binding activities and peptides that promote cell adhesion and osteogenesis. In such embodiments, the scaffold effectively forms bone material which promotes integration and healing.

In further embodiments, functionalized viruses can provide metallization (or decoration with metal nanoparticles) to the scaffold, for example metallization of a nanocellulose scaffold, for example such that layers of metal types (either the same metal type or at least two different metal types) can be provided to the scaffold. Such a scaffold may be utilised in fuel cells, batteries and conductant and catalytic materials. Viruses could be evenly distributed through a scaffold or, as discussed above, layering could be used to spatially control the distribution of modified viruses and their functionality.

As would be understood to those of skill in the art, a scaffold, for example a cellulose, in particular cellulosic material in particular a nanocellulose, scaffold structure functionalized with a virus that surface displays chemically catalytic peptides can provide a high surface area membrane for catalyzing reactions. In embodiments, scaffolds, for example cellulose derived scaffolds for example cellulosic material, in particular nanocellulose incorporating virus or nanoparticles further containing cell growth factor and cell adhesion peptides can be utilised in bone and tissue repair applications as dressings or as 3D scaffolds.

Preferred features and embodiments of each aspect of the invention are as for each of the other aspects mutatis mutandis unless context demands otherwise.

Each document, reference, patent application or patent cited in this text is expressly incorporated herein in their entirety by reference, which means it should be read and considered by the reader as part of this text. That the document, reference, patent application or patent cited in the text is not repeated in this text is merely for reasons of conciseness.

Reference to cited material or information contained in the text should not be understood as a concession that the material or information was part of the common general knowledge or was known in any country.

Throughout the specification, unless the context demands otherwise, the terms 'comprise' or 'include', or variations such as 'comprises' or 'comprising', 'includes' or 'including' will be understood to imply the includes of a stated integer or group of integers, but not the exclusion of any other integer or group of integers.

Embodiments of the present invention will now be provided by way of example only, with reference to the accompanying figures in which FIG. 1 illustrates SEM analysis carried out on nanocellulose only;

Figure 11:
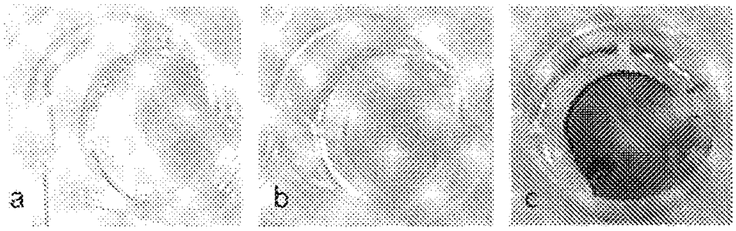

FIG. 11 illustrates the colour change observed when dried films composed of cellulose only (a) or cellulose with SPs (b) or Spherical Particle-Calf-Intestinal Alkaline Phosphatase (SP-CIP) (c) were washed with the CIP substrate (BCIP (5-bromo-4-chloro-3-indonyl-phospate) in conjunction with NBT (nitro blue tetrazolium)). Cellulose films composed of cellulose only (a) or cellulose with SPs (b) did not show any reactivity as indicated by no colour change from white to dark blue (FIGS. 11*a*, 11*b*). In contrast, a strong colour change to dark blue was detected in nanocellulose films containing the SP-CIP enzyme (FIG. 11*c*).

EXAMPLE 1

Genetic Modification of Tobacco Mosaic Virus Tobacco mosaic virus (TMV) was modified genetically such that small peptides like the metal binding and reducing peptide (MBP), (MBP; Tan, Y. N., Lee, J. Y., and Wang, D. I. C. 2010. Uncovering the design rules for peptide synthesis of metal nanoparticles. *J. Am. Chem. Soc.* 132, 5677-5686.) SEKLWWGASL (SEQ ID NO: 1), or a hydroxyapatite deposition peptide (MIP3), (MIP3; Choi, Y. S., Lee J. Y., Suh, J. S., Lee, G., Chung, C. P., Park, Y. J. 2013. The mineralization inducing peptide derived from dentin sialophosphoprotein for bone regeneration. J Biomed Mater Res A, 101(2), 590-8.) SESDSSDSDSKS (SEQ ID NO: 2), was inserted into the surface exposed regions of the coat protein. (Turpen, T. H., Reinl, S. J., Charoenvit, Y., Hoffman, S. L., Fallarme, V., Grill, L. K. 1995. Malarial epitopes expressed on the surface of recombinant tobacco mosaic virus. Nature Biotechnology, 13(1), 53-57.) and (Bendahmane, Karrer, E., Beachy, R. N. 1999. Display of epitopes on the surface of tobacco mosaic virus: impact of charge and isoelectric point of the epitope on virus-host interactions. J Mol Biol. 290(1), 9-20.). Peptide insertion did not compromise virion formation. Moreover, these viruses could be obtained to a high yield using plants (>1 g/kg fresh tissue weight).

The method can utilize restriction sites which are either already present or engineered into the nucleic acid sequence of the surface exposed regions of TMV, for example a PpuMI restriction site permits insertion of sequences into the surface exposed C-terminal end of the coat protein; or alternatively NgoMIV/BstZ17I restriction sites may be used to introduce sequences into a surface exposed loop of the coat protein which lies between 195-210 base pairs of the coat protein.

Suitable restriction enzyme digestion of the TMV vector at the region for surface display, prior to insertion of sequences of interest into this region may be carried out as below. For example, 200 ng of TMV vector was combined with 2.5 units of NgoMIV and BstZ17I and a propriety brand of 1× cut smart buffering solution (New England Biolabs; 240 County Road Ipswich, Mass.) prior to incubation at 37° C. for 4 hours. Subsequently, 20 units of New England Biolabs CIP was then added to the reaction and incubation was continued for another 3 hours at 37° C. in order to remove phosphates at the excision site. The reactions were gel electrophoresed on 1% agarose 1×TBE gels which were run at 100 v for 4 hours. After the bands on the gel were resolved the linearized plasmid was excised from the gel and the DNA was extracted using a Qiagen gel extraction kit (QIAGEN GmbH QIAGEN Strasse 1 40724 Hilden; Germany). The purified digested and dephosphorylated plasmids were then ligated to phosphorylated annealed oligonucleotide primers (see sequences below) using DNA ligase and ligase buffer as per the protocols of New England Biolabs. The annealed oligonucleotides contain complementary overhangs which permit the in-frame ligation of the sequences that correspond to the peptides of interest. This procedure generates for example a DNA sequence which when expressed in an organism or in vitro system, produces a virus coat protein that displays a functional peptide sequence of interest, with the peptide still retaining its functionality and accessibility even after self-assembly into a larger virus or virus-like structure.

MIP3 primers- (SEQ ID NO: 3)
F: 5' CCGGC TCT GAA TCT GAT TCT TCT GAT TCT GAT TCT AAG TCT GTA

(SEQ ID NO: 4)
R: 5' TAC AGA CTT AGA ATC AGA ATC AGA AGA ATC AGA TTC AGA G

MBP primers- (SEQ ID NO: 5)
F: 5' CCGGC TCTGAAAAGCTTTGGTGGGGAGCTTCTCTTGTA

(SEQ ID NO: 6)
R: 5' TAC AAAGAGAAGCTCCCCACCAAAGCTTTTCAGAG

Suitably a TMV vector used in such manipulations may contain a T7 transcriptional promoter to allow in vitro transcription, which leads to the formation of infectious RNA transcripts which can subsequently be rubbed on plants such as *Nicotiana benthamiana* to propagate the virus. Virus can be easily extracted to a high yield by finely grinding infected leaf material in the presence of aqueous buffers, which then undergoes various stages of low speed centrifugation in the presence of polyethylene glycol and salts, with the resulting pure pellet being resuspended in an appropriate phosphate buffer according to Gooding and Herbert (Gooding, G V and Herbert, T T. 1967. A simple technique for purification of tobacco mosaic virus in large quantities. Phytopathology Volume: 57 Issue: 11 Pages: 1285).

EXAMPLE 2

Preparation of Functionalized Nanocellulose Films Using Viruses

TMV modified with the MBP and MIP3 peptides were used to functionalize nanocellulose scaffold. Viscous purified nanocellulose dispersions and dispersions of cell wall particles containing nanocellulose fibres were produced from waste plant material, by different extraction techniques, wherein the plant material was treated with either NaOH treatment (as specified in WO2013/128196 for example wherein, for example root vegetable waste, such as carrot or sugar beet from existing industrial processes, can be processed to form a mixture having a concentration of between 0.1% and 10% solids content by weight in water. 0.5M sodium hydroxide (NaOH) can be added to the solution, raising and maintaining the pH of the solution at pH 14 such that the addition of the NaOH extracts a significant proportion of hemicellulose and the majority of pectin from the cellulose of the cells within the mixture. The mixture can then be heated to 90° C. for five hours and homogenised periodically during the heating period for a total of one hour with a mixer blade rotating at a rate of 11 m/s (6), followed by homogenisation for a period of five minutes, at the end of the heating period, with a mixer blade rotating at a rate of 30 m/s (8). Homogenisation separates the cells along the line of the middle lamella, then breaks the separated cells into platelets. The resultant cellulose platelets are approximately 10 times smaller than the original separated cells and the resultant mixture can then be filtered to remove the dissolved materials to a solids content of less than 8% by weight, peroxide treatment (as specified in WO2014/147392 or WO2014/147393), for example wherein 35% aqueous peroxide solution may be added in an amount of 0.5% by weight or less of the weight of herbaceous plant material (dry content) and a peroxide treatment step carried out until substantially all of the peroxide has been consumed and then terminated such that a particulate cellulose material with a viscosity of at least 2500 cps (at a 1 wt % solids concentration) is obtained) or enzyme treatment.

TMV virus stock solutions (wild type and modified) were prepared in 10 mM sodium phosphate pH7 buffer.

1. 250 μl Cellulose dispersion was mixed with 10 μl of wild type or modified TMV (22 mg/ml; total virus per reaction is 220 μg) to provide a cellulose mixture.
2. After incubation at room temperature (between 20°-25° C.) for 2 hours the cellulose dispersion was pipetted and spread onto a 1 $cm^2$ area on a flexible plastic sheet.
3. The cellulose dispersion was left to dry overnight at room temperature in a dust free location to form a dried sample.
4. The dried sample was peeled from the plastic sheet and washed several times in distilled water, prior to re-drying for analysis using electron microscopy, or for inclusion in metal or hydroxyapatite catalytic experiments.

Figure 1:
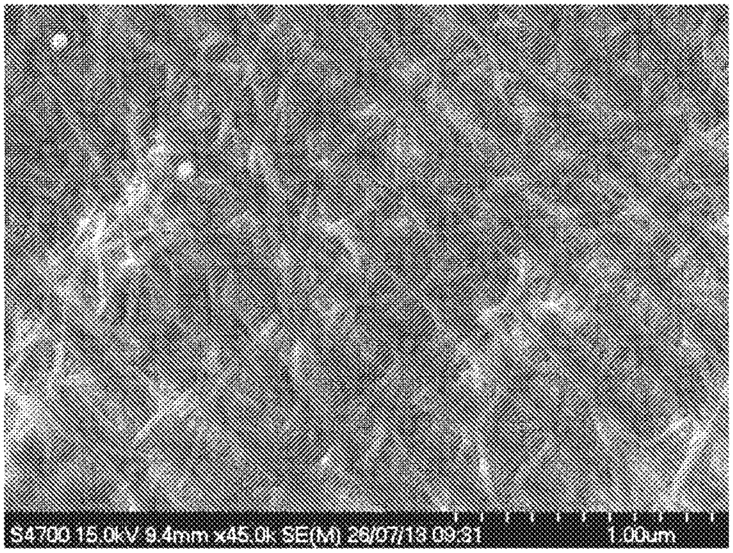
Figure 2:
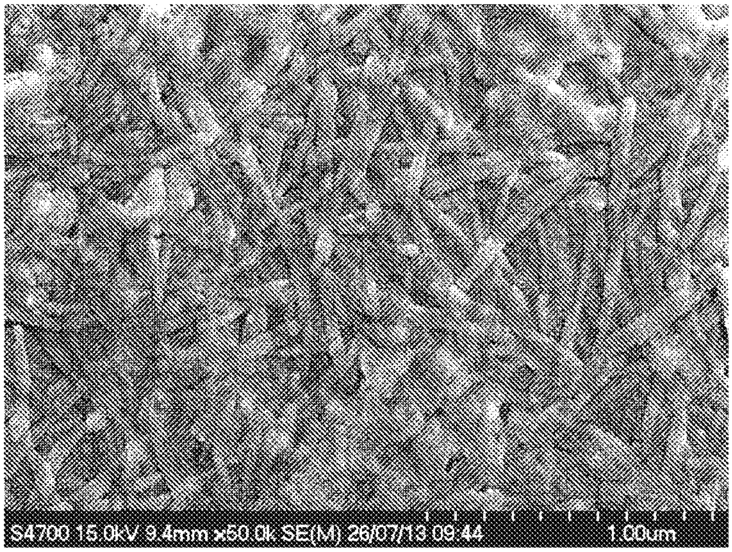
FIG. 2 illustrates SEM analysis carried out on nanocellulose functionalized with non-modified virus.

Using scanning electron microscopy (SEM) it was found that nanocellulose and nanocellulose containing particles only, formed a network of nanocellulose fibres, or a nanocellulose film or membrane (FIG. 1), whereas those samples containing TMV had significant amounts of virus displayed on the film or membrane surface (FIG. 2).

EXAMPLE 3

Testing the Preserved Immunoreactivity of TMV in the Nanocellulose Film

Figure 3:
FIG. 3 illustrates TEM cross section of immunogold labelled non-modified virus in nanocellulose (location of virus denoted by dark dots)

Tobacco mosaic virus integrated into the nanocellulose structure was cross-reactive to antibodies specific for the virus, as indicated by the localization of gold particle-antibody conjugates to the virus (FIG. 3). This demonstrates that incorporation of virus structures into the nanocellulose substrate does not compromise their immunogenic capacity. Given that viruses and virus like particles can be surface modified to display immunogenic regions from diverse pathogens (Thuenemann, E. C., Lenzi, P., Love, A. J., Taliansky, M. E., Bécares, M., Zuñiga, S., Enjuanes, L., Zahmanova, G. G., Minkov, I. N., Matic, S., Noris, E., Meyers, A., Hattingh, A., Rybicki, E. P., Kiselev, O. I., Ravin, N. V., Eldarov, M. A., Skryabin, K. G. and Lomonossoff, G. P. 2013. The use of transient expression systems for the rapid production of virus-like particles in plants. Current Pharmaceutical Design 19, 5564-5573.), it is also likely that these would be recognizable by the appropriate antibodies after incorporation into the nanocellulose network. The combination of the substrates flexibility and ease with which the virus and virus-like particles can be modified to display immunogenic regions of diverse pathogens, provides utility in production of new diagnostic devices.

After confirmation of incorporation of the virus, the utility of the virus functionalized membranes were tested in several different catalytic reactions depending on the functionalities of the virus.

EXAMPLE 4

Testing Metal Nanoparticle Formation.

Figure 4:
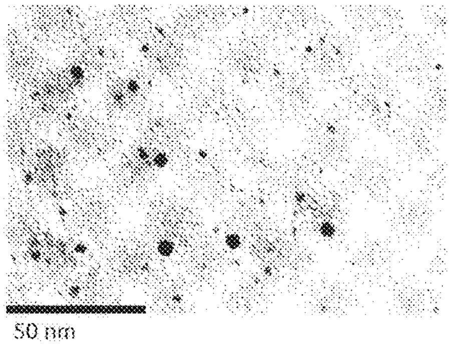
FIG. 4 illustrates silver nanoparticle formation in a TMV-MBP functionalized sample.
Figure 5:
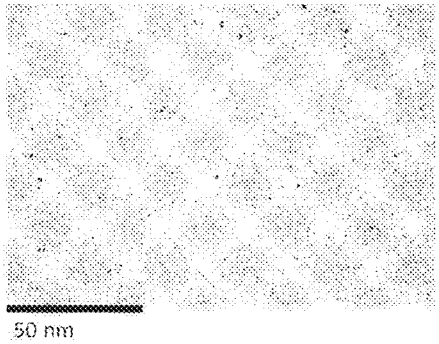
FIG. 5 illustrates silver nanoparticle formation in a non-modified TMV sample.

A TMV-MBP functionalized, washed nanocellulose film was placed in an eppendorf tube and 500 μl $AgNO_3$ (2.9×$10^{-3}$ M) metal salts were added. TEM analysis found that significant amounts of silver nanoparticles formed in the supernatant within an hour in the TMV-MBP functionalized sample (FIG. 4), with little or no formation in the non-modified TMV sample (FIG. 5).

EXAMPLE 5

Testing Hydroxyapatite Deposition

Nanocellulose films were produced with TMV-MIP3 or TMV as above except that double the amount of virus was used (440 μg per 250 μl of nanocellulose).

Figure 6:
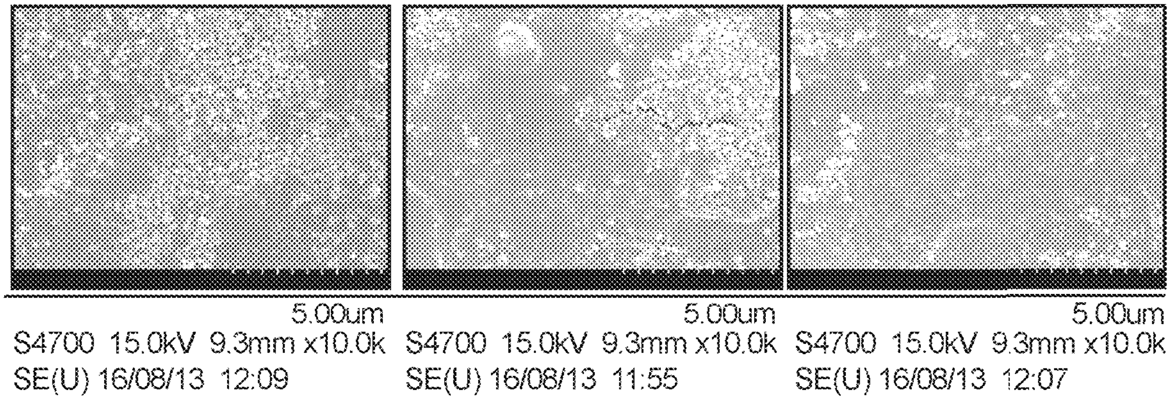
FIG. 6 illustrates an SEM of a nanocellulose membrane exposed to hydroxyapatite precursors.
Figure 7:
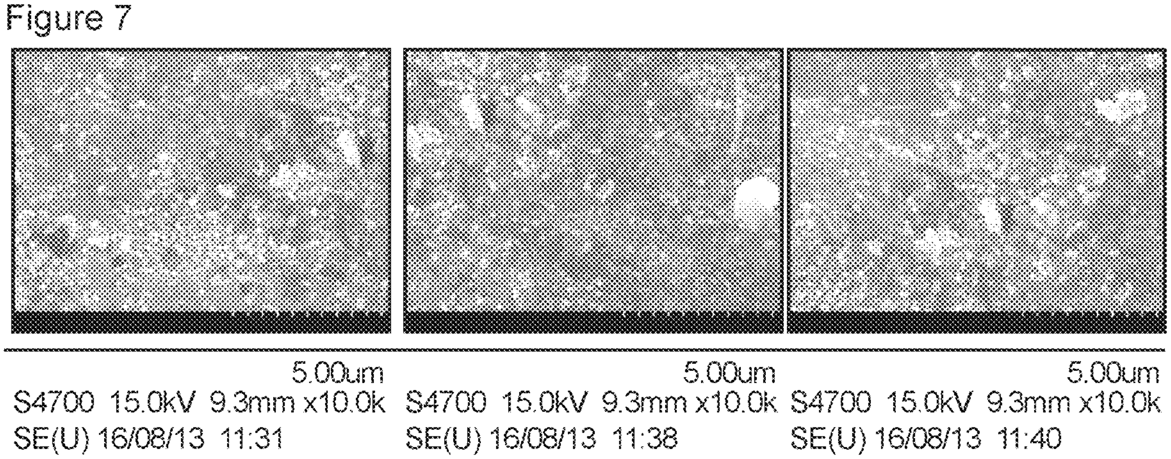
FIG. 7 illustrates SEM analysis carried out on nanocellulose functionalized with unmodified virus after treatment with hydroxyapatite precursors.
Figure 8:
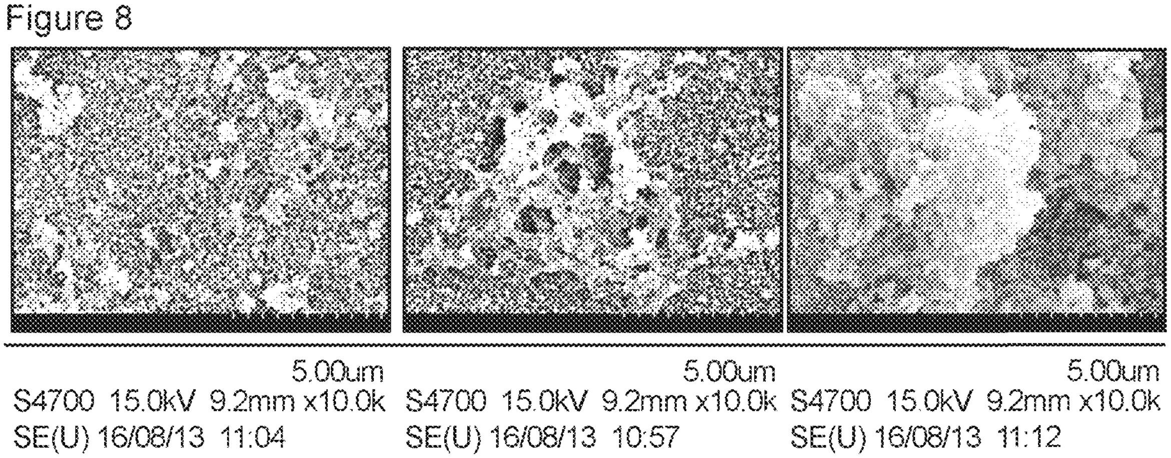
FIG. 8 illustrates SEM analysis carried out on nanocellulose functionalized with MIP3 modified virus after treatment with hydroxyapatite precursors.

The washed membranes were incubated for 17 hours in 100 mM $CaCl_2$ (pH 4.83). Subsequently the membranes were washed in distilled water and incubated in 60 mM $Na_2HPO_4$ (pH 8.36) with slight agitation. The process of washing and sequentially incubating with the HA precursors ($CaCl_2$ and $Na_2HPO_4$) was repeated once more, with a final wash step prior to a final drying. SEM analysis was carried out, and it was found that the nanocellulose only (FIG. 6) and the nanocellulose functionalized with non-modified virus (FIG. 7) which had been exposed to HA precursors had very little HA deposition. In contrast, significant HA deposition was observed with the nanocellulose which had been functionalized with the TMV-MIP3 (FIG. 8).

Production of Structures Formed from Viral Protein Components for Display of Whole Proteins/Enzymes A new platform for the surface presentation of peptides or whole proteins/enzymes was determined to be generated by thermal remodelling of plant viruses, such as TMV. Heating of TMV rod-shaped viruses at 94° C. for 5 minutes leads to formation of nanoscale spherical particles (SPs) (patent WO 2012078069 A1), which are RNA-free and can bind any peptide or whole protein/enzyme for formation of functional complexes. TMV (concentration 1 mg/ml) was used to prepare SPs about 200-500 nm in diameter. SPs in solution (0.1 mg in 100 μl) were mixed with Calf-Intestinal Alkaline Phosphatase (CIP) (0.02 mg in 6 μl); the mixture was incubated for 1 hour at room temperature and then centrifuged (2300 g, 5 min) to separate the unbound protein. The obtained pellet was resuspended in 100 μl of milli-Q water. The SPs decorated with CIP (SP-CIP) were mixed with 100 μl of nanocellulose suspension and left to dry at room temperature into thin films. Thin films comprising cellulose alone or cellulose containing the same amount of SPs were used as negative controls.

The dried cellulose films were washed with water several times. The CIP substrate (BCIP (5-bromo-4-chloro-3-indonyl-phospate) in conjunction with NBT (nitro blue tetrazolium)) was added to the washed cellulose membranes and colour changes were observed. Films composed of cellulose only or cellulose with SPs did not show any reactivity as indicated by no colour change from white to dark blue (FIG. a, b). In contrast, a strong colour change to dark blue was detected in nanocellulose films containing the SP-CIP enzyme (FIG. c), demonstrating that enzymatic activity in the nanocellulose films was preserved even after drying and washing. Thus, incorporation of platforms decorated with enzymes, confers functionality to the nanocellulose matrix which is stable.

EXAMPLE 6

Paint Study, Using Nanocellulose Containing Particles to Make Paint Formulations Two sets of paint formulations were made up (see Tables 1 and 2 below). One was made using an epoxy resin system and the other using an acrylic resin system. For each set a number of batches were made containing different amounts of Curran (nanocellulose containing particles) produced by the method outlined in the rheological formulation paragraphs below. The weight of all additives in both the epoxy and acrylic formulations was kept constant from one batch to the next, except for water and viscosity modifier. The weight of viscosity modifier was varied from one batch to another, to test the effects of different addition levels on the formulation viscosity. In order to keep total formulation weight constant the weight of water added to a batch was also adjusted depending upon the addition level of the viscosity modifier, so that weight of water plus the viscosity modifier was constant from one batch to another.

The cellulose-containing particles had been pressed to reduce water content to 25% solids then grated using a parmesan cheese grater into a coarse powder. The ingredients of each formulation were mixed together at room temperature using a Dispermat paint mixer, with saw tooth blade of 4 cm diameter rotated at 3000 rpm. Mixing was carried out for 1 hr to ensure that all ingredients were fully dispersed. The mixed formulations were allowed to stand for 1 day. Then the viscosity of each sample was scanned over a range of shear rates using a rheometer.

For the epoxy formulation a bench mark, which was a well known Bentonite clay rheology modifier, was used to allow comparison with the cell wall material. This was mixed into the formulation at a concentration of 0.25% by total formulation weight.

Similarly for the acrylic formulation a suitable bench mark was used for comparison, which was an Acrysol associative thickener. This was mixed into the formulation at 0.6% of total formulation weight.

TABLE 1

| Material<br>Epoxy Resin Component | % | g |
|---|---|---|
| Beckopox EP 2384w/57WA | 20.30 | 101.50 |
| Water | 8.71 | 43.53 |
| Cell wall material: powder | 0.09 | 0.47 |
| Additol VXW-6393 Defoamer | 0.40 | 2.00 |
| Additol VXW-6208/60 | 1.00 | 5.00 |
| RO-4097 Red Iron Oxide | 7.00 | 35.00 |
| Halox SZP-391 Anti-Corrosive Pigment | 4.60 | 23.00 |
| Barium Sulphate | 9.20 | 46.00 |
| Minelco Wollastonite Powder MW50 | 13.90 | 69.50 |
| Zeeosphere 400 Ceramic Microspheres | 9.30 | 46.50 |
| 325 mesh Water Ground Mica | 0.70 | 3.50 |
| Beckopox EP 2384w/57WA | 20.30 | 101.50 |

TABLE 1-continued

| Material<br>Epoxy Resin Component | % | g |
|---|---|---|
| Additol VXW-6393 Defoamer | 0.40 | 2.00 |
| BYK 348 | 0.40 | 2.00 |
| Cotrol AMB ammonium Benzoate (10% in Water) | 3.70 | 18.50 |
| | 100.00 | 500.00 |

Figure 9:
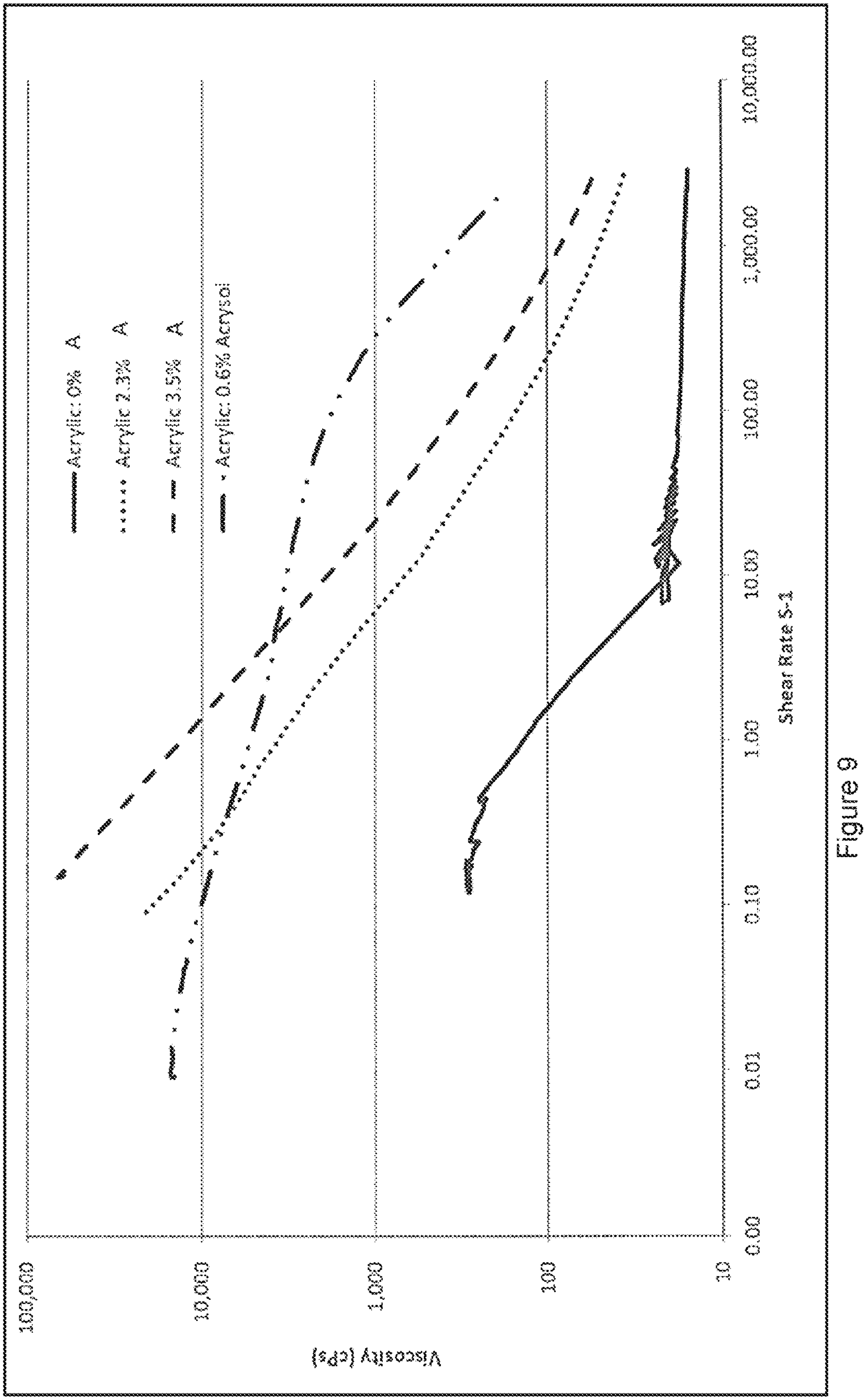
FIG. 9 illustrates shear rates s-1 against viscosity (CP).

A graph showing viscosity as a function of shear rate for an epoxy paint formulation with varying amounts of cellulose-containing particles added as a viscosity modifier (here labelled A) and compared to a Bentonite clay viscosity modifier (labelled Bentone E W) is shown in FIG. 9. It can be seen that the use of 0.15% cellulose-containing particles generate higher viscosities in the epoxy formulation that the Bentonite clay, particularly at low shear rates.

TABLE 2

| Acrylic/low PVC formulation | | |
|---|---|---|
| Material | % | g |
| Water | 15.57 | 93.42 |
| Cell wall material: 2.3% Powder | 2.33 | 13.98 |
| Propylene Glycol | 2.00 | 12.00 |
| Pat-Add AF16 | 0.20 | 1.20 |
| Pat-Add DA 420 | 0.60 | 3.60 |
| Pat-Add DA 202 | 0.40 | 2.40 |
| Kemira RDI-S | 22.20 | 133.20 |
| Neocryl XK 98 | 55.30 | 331.80 |
| Pat Add AF 16 | 0.10 | 0.60 |
| Parrmetol A 23 | 0.30 | 1.80 |
| Pat-Add COAL 77 | 1.00 | 6.00 |
| Total | 100.00 | 600.00 |

Figure 10:
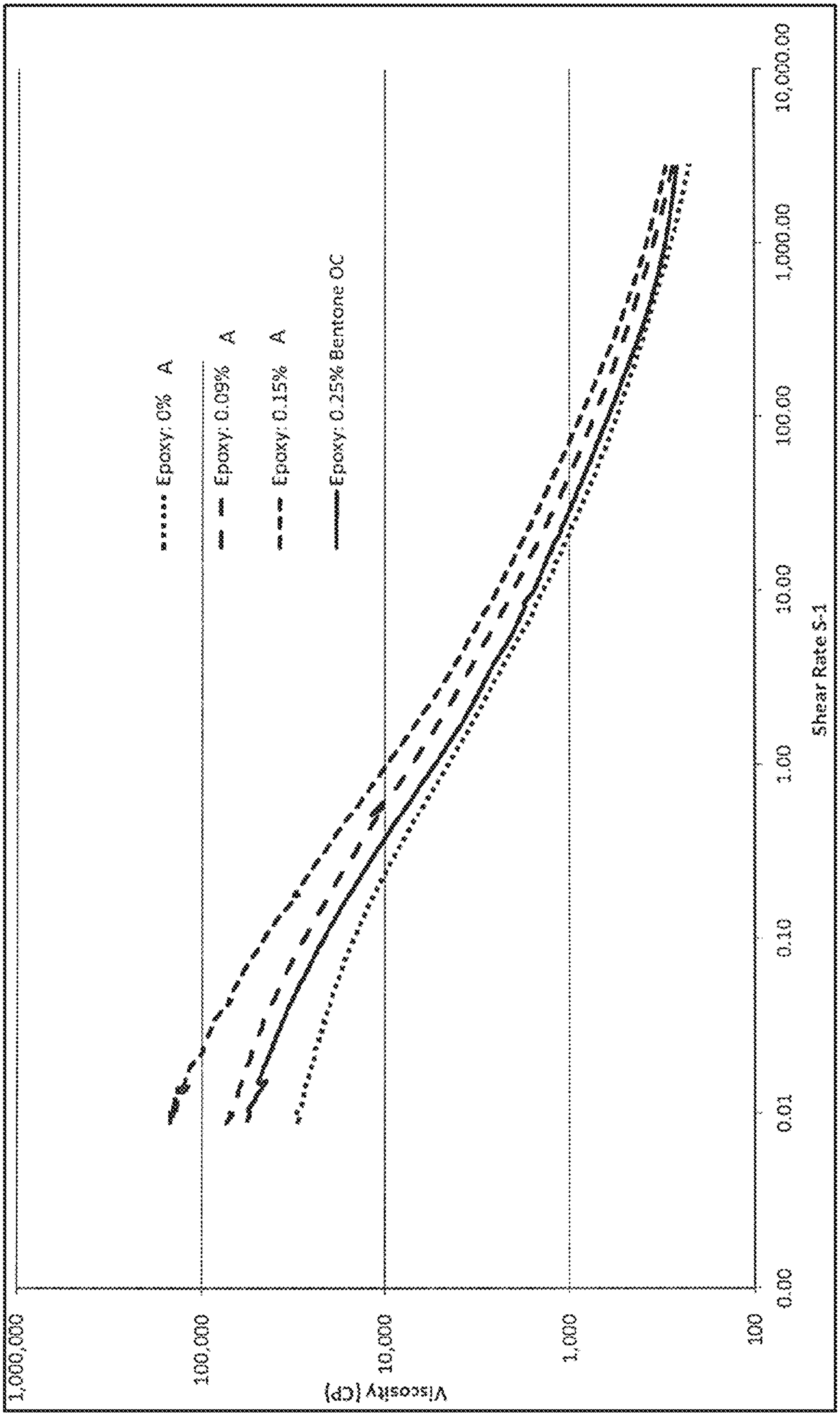
FIG. 10 illustrates shear rates s-1 against viscosity (CP).

A graph showing viscosity as a function of shear rate for an acrylic paint formulation with varying amounts of cellulose-containing particles added as a viscosity modifier (here labelled A) and compared to an associative thickener acting as a viscosity modifier (Acrysol) is shown in FIG. 10 This data shows that the cellulose-containing particles are more shear thinning than the Acrysol and is particularly effective at giving high viscosity at low shear rates.

EXAMPLE 7

Cementious Materials/Concrete—Using Nanocellulose Containing Particles as an Additive in Concrete The cellulose particulate material produced by the process described in the Rheological formulation section herein, was tested for its suitability in composite materials, particularly cementitious materials such as concrete and mortar.

The cellulose particulate material was incorporated into a mortar mix in amounts of 1 wt %, 5 wt % and 10 wt % as set out below. The mortar used was a decorative mortar called Enduit Béton Coloré available from Mercardier.

Composition:

4.3 kg cement powder 1 kg acrylic resin binder 1 wt % or 5 wt % cellulose particulate material (CPM)

The indentation strength of the composite material was tested using a 2 mm thick sample of material. The test used a 62.5 MPa punch with a 1 cm diameter punch die. The results are shown in Table 3 below:

TABLE 3

| | Results in MPa | | | |
|---|---|---|---|---|
| Composition | Sample 1 | Sample 2 | Sample 3 | Average |
| EBC | 29.5 | 26.5 | 29.5 | 28.5 |
| EBC + 1% CPM | 36.5 | 37.5 | 34.5 | 36.17 |
| EBC + 5% CPM | 30.5 | 35 | 31.5 | 32.33 |
| EBC + 10% CPM | 29 | 30 | 26.5 | 28.5 |

This data shows that inclusion of up to 5 wt % of the cellulose particulate material described herein led to an improvement in the strength of the material, demonstrating that the cellulose particulate material is able to strengthen or reinforce inorganic composite materials such as concrete.

EXAMPLE 8

Paper Compositions—Using Nanocellulose Containing Particles as Additives to Paper A paper composition comprising differing amounts of the cellulose particulate material (CPM) produced by the process described in the rheological material formulation section below, was tested for opacity and porosity.

Inclusion of the cellulose particulate material described herein decreased porosity relative to a base paper formed from a standard cellulose. Decreasing porosity of a paper composition provides advantages for food, cosmetic and fragrance-type packaging where permeation of gases, microbes and other substances is undesirable.

From the above examples, it can be seen that the cellulose particulate materials described herein, and the processes for producing such cellulose particulate materials find utility in many different applications.

Examples of forming and analysing cellulosic scaffold compositions of the invention are now described.

EXAMPLE 9

Composite Formulation—Using Nanocellulose Containing Particles to Make Composites 30 kg of Carrots were peeled, chopped into pieces and then added into a cooking pot with an equal weight of tap water and cooked for 3 hrs at 95° C. until soft. The material was then homogenised using a silverson FX in-tank homogenisaser. Coarse medium and fine heads were used on the homogeniser to gradually reduce particle size until an average particle size of around 100 microns was achieved. Sodium hydroxide was then added in a ratio of 2 parts NaOH to 1 part of plant material solids. The material was then re-heated to 90° C. while stirring continually. The stirred material was held at 90° C. for 8 hrs. The material was then cooled and filtered using a gravity filter. Several washes of clean water were put through the material until the pH had reached 7. The material was then mixed with Polyvenyl alcohol/acetate and water based epoxy resin+hardener in a ratio of 85% plant material, 10% epoxy+hardener and 5% PVA (on a solids basis). The PVA was mixed in first by adding the liquid PVA (containing around 70% water) to the plant material, mixing thoroughly for 30 minutes and then pressing the material to 7.7% solids (most of the PVA remains trapped in the plant mix during this pressing). The pressing was carried out by placing the material in a porous bag of filter material and pressing it in a hydraulic filter press between 2 metal plates until the solids in the bag reached 7.7%. Water based epoxy resin (either a dispersion or an emulsion) was then mixed into the plant material+PVA using a dough mixer. Additional water can be added depending upon the application. The resulting material when dried shrinks and forms a hard biocomposite material. Sheets can be formed if the plant material+PVA+Epoxy and hardener+water is liquid and this liquid is poured into plastic trays and the material dried.

As would be understood by those of skill in the art, the plant material to be mixed with the PVA epoxy and hardener can be produced by alternative treatments. Other examples include but are not limited to, treatment of the plant material with hydrogen peroxide at 90° C. or by treatment of the plant material with enzymes.

EXAMPLE 10

Rheological Material Formulation—Using Nanocellulose Containing Particles to Make a Rheological Modifier 900 g of sugar beet pellets were washed and hydrated by adding them to warm water, with dirty water being drained through a sieve. This sugar beet hydrate was placed in a large bucket in excess water and agitated before being scooped out with a colander and washed with water, to ensure that no stones/grit enter the next stage of processing.

The washed sugar beet was cooked for 3 hours at 100° C., before being homogenised using a Silverson FX homogeniser fitted with initially coarse stator screens and moving down to the small holed emulsifier screen (15 min process time for each screen). The solids were measured using an Oxford solids meter and the mixture adjusted to 2% solids by addition of clean water.

The mix was then placed in a 25 litre glass reaction vessel and the dry solids content in the vessel calculated. Peroxide based on ratio of aqueous peroxide solution (at 35%) to the dry solids of 0.25:1 was added when the mix was heating. The temperature was maintained for 2 hours at 90° C. (once it reaches 90° C.), by which time the pH dropped from around 5 to 3.5.

The reaction liquid was then removed from the vessel and washed prior to bleaching Bleaching was then carried out by re-suspending the washed material in clean water and placing it back in the vessel. Bleaching was performed at 60° C., with a 2:1 bleach (2 parts of bleach solution with 10% active chlorine to 1 part solids, for 30 minutes).

The material was then washed and homogenised for 30 minutes on the fine slotted stator screen of the Silverson FX homogeniser The material is then drained through a filter and pressed between absorbent cloths to a desired final solids content. Resuspension of the solids in water at 1 wt % solids resulted in a viscosity (measured as previously described) of 4600 cps.

EXAMPLE 11

Analysis of the Cellulose Containing Particles (Produced by Peroxide Extraction as Described in Example 10 and WO2014/147392 or WO2014/147393) Using Acid Hydrolysis Extraction Dry material from three stages of the process (start; after peroxide treatment; after sodium hypochlorite treatment) was analysed for extractable monosaccharide/polysaccharide content. The starting plant materials tested were sugar beet and carrot.

The test procedure was carried out according to the standard two-step protocol below, which is based on separation of monosaccharides and oligosaccharides from polysaccharides by boiling the sample in an 80% alcohol solution. Monosaccharides and oligosaccharides are soluble in alcoholic solutions, whereas polysaccharides and fibre are insoluble. The soluble components can be separated from the insoluble components by filtration or centrifugation. The two fractions (soluble and insoluble) can then be dried and weighed to determine their concentrations.

The dried materials can then be used for analysis by HPLC, following acid hydrolysis.

(i) Separation of Alcohol Soluble and Insoluble Components

Materials

Dry samples

80% Ethanol

Compressed Nitrogen

Method

For each material sample, 50 mg was extracted three times with 5 ml of 80% ethanol, by boiling the samples in capped glass tubes in 95° C. water bath for 10 min each. After each extraction, the tubes were centrifuged at 5000×g for 5 min, and the supernatants of the three extractions combined for sugar analysis.

The residue and supernatant are oven dried prior to acid hydrolysis. Acid hydrolysis using trifluoroacetic acid degrades pectins, hemicelluloses and highly amorphous regions of cellulose, while acid hydrolysis using 72% (w/v) sulphuric acid degrades all polysaccharides with the exception of highly crystalline regions of cellulose.

(ii)(a) Analysis of Matrix Polysaccharides—Trifluoroacetic Acid Hydrolysis

Materials

Dry samples

Screw cap tubes

2M Trifluororoacetic acid=11.4 g in 50 ml (or 3 ml 99.5% TFA and 17 ml $dH_2O$)

Compressed Nitrogen

Monosaccharide standards

Standard sugar mixture of three monosaccharides (glucose, fructose, xylose). Each sugar is in a 10 mM stock solution (100×). The preparation of the standards is done by pipetting 250, 500, and 750 µl in screw cap vials and evaporating to dryness. Proceed to hydrolysis in the same way as with the samples.

Method

Day 1

Weigh 5 mg of the alcohol insoluble fraction from step (i) in screw cap tubes

Dry all the samples and monosaccharide standards (250 µl, 500 µl, 750 µl)

Day 2

In the fume hood, hydrolyse by adding 0.5 ml 2 M TFA. Flush the vials with dry nitrogen, place the cap, and mix well. Wipe nitrogen nozzle with ethanol tissue between samples to prevent contamination.

Heat the vials at 100° C. for 4 h and mix several times during hydrolysis.

Evaporate completely in centrifugal evaporator or under a nitrogen flush with fume extraction overnight.

Day 3

Add 500 µl of propan-2-ol, mix, and evaporate.

Repeat

Resuspend the samples and standards in 200 µl of $dH_2O$. Mix well.

Centrifuge and transfer the supernatant into a new tube.

Filter supernatant through 0.45 µm PTFE filters prior to HPLC analysis.

(ii)(b) Analysis of Matrix Polysaccharides—Sulphuric Acid Hydrolysis

Materials

Sulphuric acid 72% (w/v) (AR)

Barium hydroxide (150 mM)

Bromophenol blue (1% solution in water)

0.45 µm filters

SPE reverse phase (styrene divinylbenzene); e.g. Strata-X 30 mg, 1 ml volume.

Method

Weight accurately 4 mg of the alcohol insoluble fraction from step (i) into a 2.0 ml screw-top microcentrifuge tube. Alternatively use the dried residue from the matrix sugar digestion.

Add 70 µl of 72% (w/v) sulphuric acid to the screw-top vial. Mix, until solids are dispersed/dissolved.

Incubate in a water bath at 30° C. for 2 hours. Mix samples every 15 minutes.

Add water to reduce the sulphuric acid concentration to 4.6% (w/w)—add 1530 µl water.

Mix well and heat in a block heater at 121° C. for 4 hours. Vortex every 30 minutes.

Cool to room temperature. (Samples may be stored in fridge for up to 2 weeks at this point).

Take 300 µl into a new tube, add 1 µl of 1% bromophenol blue. Partially neutralise by the addition of 0.8 ml 150 mM barium hydroxide. Finish by adding barium carbonate powder. The indicator goes blue.

Centrifuge to eliminate the precipitated barium sulphate (10 min at 10000×g). Transfer supernatant to a new tube. Freeze thaw to finish precipitation and repeat centrifugation (total volume 1050 µl).

Prior to HPLC, the samples (700 µl aliquot) are passed on a reverse phase column (e.g. strata X 30 mg) and filtered through a 0.45 µm filter.

The results of these analyses, with respect to xylose content and glucose content are shown in Table 4. Quantitative data can be obtained by injection of a known amount of a reference monosaccharide, for example glucose or xylose, as is routine in the art, as well as comparative materials such as those disclosed in WO2014017911 (Examples CelluComp 8 to 10).

Although the invention has been particularly shown and described with reference to particular examples, it will be understood by those skilled in the art that various changes in the form and details may be made therein without departing from the scope of the present invention.

TABLE 4

| Sample | Material | Process | Sample taken for TFA hydrolysis (mg) | Peak area | xylose (mg) | % xylose release |
|---|---|---|---|---|---|---|
| Cellucomp 1 | Sugar Beet | Start Material | 4.8 | 30274 | 0.955 | 19.90 |
| Cellucomp 2 | Sugar Beet | Peroxide Process | 5.7 | 2880 | 0.089 | 1.56 |
| Cellucomp 3 | Sugar Beet | Full Process | 5.1 | 3281 | 0.102 | 2.00 |
| Cellucomp 4 | Sugar Beet | Full Process with extra wash | 5.4 | 3161 | 0.098 | 1.82 |
| Cellucomp 5 | Carrot | Start Material | 5.4 | 3230 | 0.100 | 1.86 |
| Cellucomp 6 | Carrot | Peroxide Process | 4.9 | 1334 | 0.040 | 0.82 |

TABLE 4-continued

| | | | | | | |
|---|---|---|---|---|---|---|
| Cellucomp 7 | Carrot | Full Process | 4.7 | 1530 | 0.046 | 0.99 |
| Cellucomp 8 | Comparative Example (Carrot) | NaOH + heat | 5.6 | 1021 | 0.030 | 0.54 |
| Cellucomp 9 | Comparative Example (Carrot) | Cellucomp 8 followed by bleach | 4.6 | 1302 | 0.039 | 0.85 |
| Cellucomp 10 | Sugar Beet (low viscosity) | Full process | 4.9 | 1119.3 | 0.033 | 0.68 |

| Sample | Material | Process | Sample taken for H2SO4 hydrolysis (mg) | Peak area | glucose (mg) | % glucose release |
|---|---|---|---|---|---|---|
| Cellucomp 1 | Sugar Beet | Start Material | 4.8 | 351 | 0.353 | 7.31 |
| Cellucomp 2 | Sugar Beet | Peroxide Process | 5.7 | 1121 | 0.739 | 12.99 |
| Cellucomp 3 | Sugar Beet | Full Process | 5.1 | 1830 | 1.098 | 21.57 |
| Cellucomp 4 | Sugar Beet | Full Process with extra wash | 5.4 | 1654 | 1.012 | 18.71 |
| Cellucomp 5 | Carrot | Start Material | 5.4 | 858 | 0.605 | 11.26 |
| Cellucomp 6 | Carrot | Peroxide Process | 4.9 | 1525 | 0.948 | 19.29 |
| Cellucomp 7 | Carrot | Full Process | 4.7 | 1724 | 1.044 | 22.26 |
| Cellucomp 8 | Comparative Example (Carrot) | NaOH + heat | 5.6 | 3578 | 1.987 | 35.43 |
| Cellucomp 9 | Comparative Example (Carrot) | Cellucomp 8 followed by bleach | 4.6 | 2595 | 1.489 | 32.33 |
| Cellucomp 10 | Sugar Beet (low viscosity) | Full process | 4.9 | 2247 | 1.311 | 26.76 |

The invention claimed is:

1. A nanocomposite material comprising:

a) a nanocellulose scaffold, wherein the nanocellulose scaffold is a non-virus scaffold, and wherein the nanocellulose scaffold comprises a nanocellulose material and, cellulose platelets; and b) at least one virus particle, virus-like particle, or structure formed from virus components, wherein the at least one virus particle, virus-like particle, or structure formed from virus components comprises the coat protein of the tobacco mosaic virus, wherein the at least one virus particle, virus-like particle or structure formed from virus components is modified to provide surface displayed functional peptides, whole proteins, or enzymes on the surface of the virus particle, virus-like particle, or structure, wherein the at least one virus particle or virus-like particle is bound to the nanocellulose scaffold wherein the cellulose platelets comprise at least 60% cellulose by dry weight, less than 10% pectin by dry weight, and at least 5% hemicellulose by dry weight, wherein the hemicellulose comprises xyloglucans, xylans, mannans and glucomannans.

2. The nanocomposite material of claim 1, wherein the nanocellulose material is selected from nanofibrillated cellulose, cellulose nanoparticles, and cellulose nanocrystals.

3. The nanocomposite material of claim 1, wherein the nanocellulose scaffold comprises plant cell components selected from hemicellulose, pectin, and protein.

4. The nanocomposite material of claim 1, wherein the nanocellulose scaffold is a 2-dimensional structure selected from a film-like layer, web-like layer, or cross-linked fibre matrix.

5. The nanocomposite material of claim 1, wherein the nanocellulose scaffold is formed by a first layer of a 2-dimensional scaffold and a second layer of a 2-dimensional scaffold formed over the first layer to form a multi-layer or laminate structure.

6. The nanocomposite material of claim 1, wherein the nanocellulose scaffold further comprises at least one of carbon fibre, carbon nanotubes, glass fibres, silk fibres, aramid fibres, or natural fibres comprising coir, hemp, flax, jute, wood fibre, sisal, straw, and cellulose.

7. The nanocomposite material of claim 1, wherein the nanocellulose scaffold further comprises a plurality of cellulose fragments made up of a network of cellulose nanofibres/microfibrils, at least one hydrophilic binder located within the network of cellulose nanofibres/microfibrils and at least one hydrophobic binder arranged to interact with the hydrophilic binders so as to encapsulate the plurality of cellulose fragments.

8. The nanocomposite material of claim 1, wherein the nanocellulose scaffold further comprises a biocomposite material reinforced with a plurality of fibres wherein the biocomposite material comprises at least one cellulose fragment made up of a network of cellulose microfibrils, at least one hydrophilic binder located within the network of cellulose microfibrils/nanofibers and at least one hydrophobic binder arranged to interact with the at least one hydrophilic binder so as to encapsulate the at least one cellulose fragment.

9. The nanocomposite material of claim 1, wherein the virus particle or virus-like particle or structure formed from virus protein components is a nanoparticle formed from reduction of metal by the functional peptides on the surface of the virus particle or virus-like particle or structures formed from virus protein components.

10. The nanocomposite material of claim 1, wherein the virus particle, virus-like particle or structure formed from virus protein components or nanoparticle formed therefrom is a plant virus, non-enveloped animal virus or bacteriophage.

11. The nanocomposite material of claim 1, wherein the virus particle, virus-like particle or structure formed from virus protein components or nanoparticle formed therefrom is a plant virus.

12. The nanocomposite material of claim 1, wherein the surface displayed peptides are metal binding or reducing peptides capable of binding or reducing metal ions to provide a metallic nanoparticle.

* * * * *